US011235043B2

(12) United States Patent
Lyerly et al.

(10) Patent No.: US 11,235,043 B2
(45) Date of Patent: *Feb. 1, 2022

(54) VACCINES AGAINST ANTIGENS INVOLVED IN THERAPY RESISTANCE AND METHODS OF USING SAME

(71) Applicant: Duke University, Durham, NC (US)

(72) Inventors: Herbert K. Lyerly, Durham, NC (US); Michael A. Morse, Durham, NC (US); Takuya Osada, Durham, NC (US); Timothy M. Clay, Waterloo (BE); Zachary C. Hartman, Durham, NC (US)

(73) Assignee: Duke University, Durham, NC (US)

( * ) Notice: Subject to any disclaimer, the term of this patent is extended or adjusted under 35 U.S.C. 154(b) by 294 days.

This patent is subject to a terminal disclaimer.

(21) Appl. No.: 15/962,824

(22) Filed: Apr. 25, 2018

(65) Prior Publication Data

US 2018/0311329 A1    Nov. 1, 2018

Related U.S. Application Data

(63) Continuation of application No. 14/373,103, filed as application No. PCT/US2013/022396 on Jan. 21, 2013, now Pat. No. 9,956,276.

(60) Provisional application No. 61/588,449, filed on Jan. 19, 2012.

(51) Int. Cl.
| A61K 39/00 | (2006.01) |
| A61K 31/517 | (2006.01) |
| C07K 16/32 | (2006.01) |
| A61K 39/395 | (2006.01) |
| A61K 45/06 | (2006.01) |

(52) U.S. Cl.
CPC .... *A61K 39/001106* (2018.08); *A61K 31/517* (2013.01); *A61K 39/3955* (2013.01); *A61K 45/06* (2013.01); *C07K 16/32* (2013.01); *A61K 2039/505* (2013.01); *A61K 2039/507* (2013.01); *A61K 2039/5256* (2013.01); *A61K 2039/53* (2013.01); *A61K 2039/585* (2013.01); *C07K 2317/73* (2013.01); *C07K 2317/734* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| 6,734,172 | B2 | 5/2004 | Scholler et al. |
| 8,445,268 | B2 | 5/2013 | Lee et al. |
| 8,846,080 | B2 | 9/2014 | Biemans et al. |
| 9,216,229 | B2 | 12/2015 | Brown et al. |
| 9,226,959 | B2 | 1/2016 | Kramps et al. |
| 9,956,276 | B2 | 5/2018 | Lyerly et al. |
| 10,487,143 | B2 * | 11/2019 | Lyerly ............... C12N 15/8613 |
| 2003/0143568 | A1 | 7/2003 | Singer et al. |
| 2003/0228606 | A1 | 12/2003 | Tatarewicz et al. |
| 2003/0232350 | A1 | 12/2003 | Afar et al. |
| 2004/0253606 | A1 | 12/2004 | Aziz et al. |
| 2005/0266409 | A1 | 12/2005 | Brown et al. |
| 2008/0057064 | A1 | 3/2008 | Zhou |
| 2009/0214518 | A1 | 8/2009 | Buckanovich et al. |
| 2010/0055093 | A1 | 3/2010 | Shepard et al. |
| 2010/0279399 | A1 | 11/2010 | Robins et al. |
| 2011/0281748 | A1 | 11/2011 | Singh et al. |
| 2012/0014984 | A1 | 1/2012 | Shahabi |
| 2014/0017259 | A1 | 1/2014 | Aurisicchio et al. |
| 2014/0221329 | A1 | 8/2014 | Cronin et al. |
| 2014/0377261 | A1 | 12/2014 | Lyerly et al. |
| 2015/0047065 | A1 | 2/2015 | Brack et al. |
| 2015/0258099 | A1 | 9/2015 | Hager et al. |
| 2018/0092989 | A1 | 4/2018 | Lyerly et al. |
| 2018/0094050 | A1 | 4/2018 | Lyerly et al. |
| 2018/0282736 | A1 * | 10/2018 | Lyerly ............... A01K 67/0278 |
| 2019/0022204 | A1 * | 1/2019 | Lyerly ............... A61K 39/001106 |

FOREIGN PATENT DOCUMENTS

| WO | WO 2001/38576 | 5/2001 |
| WO | WO 2003/080835 | 10/2003 |
| WO | WO 2008/049930 | 5/2008 |
| WO | WO 2011/060260 | 5/2011 |

(Continued)

OTHER PUBLICATIONS

Abd El-Rehim, DM et al. "Expression and co-expression of the members of the epidermal growth factor receptor (EGFR) family in invasive breast carcinoma." (2004) Br J Cancer 91:1532-42.
Agus, DB et al. "Targeting ligand-activiated ErbB2 signaling inhibits breast and prostate tumor growth." (2002) 2:127-37.
Amalfitano A, Hauser MA, Hu H, Serra D, Begy CR, Chamberlain JS. Production and characterization of improved adenovirus vectors with the E1, E2b, and E3 genes deleted. J Virol. 1998;72(2):926-33.
Alimandi M et al. "Cooperative signaling of ErbB3 and ErbB2 in neoplastic transformation and human mammary carcinomas." (1995) Oncogene 10:1813-21.

(Continued)

*Primary Examiner* — Peter J Reddig
(74) *Attorney, Agent, or Firm* — Quarles & Brady LLP

(57) ABSTRACT

Methods of reducing, the likelihood of a cancer or precancer developing resistance to a cancer therapeutic or prevention agent are provided herein. The methods include administering the cancer therapeutic or prevention agent and a vaccine comprising a polynucleotide encoding a polypeptide whose expression or activation is correlated with development of resistance of the cancer or precancer to the cancer therapeutic or prevention agent to a subject. The vaccine may include a polynucleotide encoding a HER3 polypeptide. Methods of using the vaccine including the polynucleotide encoding the HER3 polypeptide to treat a cancer or precancer are also provided.

17 Claims, 13 Drawing Sheets

Specification includes a Sequence Listing.

(56) References Cited

FOREIGN PATENT DOCUMENTS

| WO | WO 2011/146568 | 11/2011 |
|---|---|---|
| WO | WO 2011/154863 | 12/2011 |
| WO | WO 2012/125864 | 9/2012 |
| WO | WO 2013/056178 | 4/2013 |
| WO | WO 2013/110030 | 7/2013 |
| WO | WO 2016/007499 | 1/2016 |
| WO | WO 2016/007504 | 1/2016 |
| WO | WO 2017/120576 | 7/2017 |

OTHER PUBLICATIONS

Amin, DN et al. "Resiliency and vulnerability in the HER2-HER3 tumorigenic driver." (2010) Sci Transl Med 2:16-17.
Amin, DN et al. "The role of HER3, the unpretentious emmber of the HER family, in cancer biology and cancer therapuetics." (2010) Semin Cell Dev Biol 2010:8.
Arteaga et al.. Treatment of HER2-positive breast cancer: current status and future perspectives. Nature Reviews Clinical Oncology, 9: 16-32, 2012.
Atkins, MB et al. "Phase I evaluation of intravenous recombinant human interleukin 12 in patients with advanced malignancies." (1997) Clin Cancer Res 3:409-17.
Begnami MD, Fukuda E, Fregnani JH, Nonogaki S, Montagnini AL, da Costa WL, Jr., et al. Prognostic implications of altered human epidermal growth factor receptors (HERs) in gastric carcinomas: HER2 and HER3 are predictors of poor outcome. J Clin Oncol. 2011;29(22):3030-6.
Ben-Kasus, T. et al. "Persistent elimination of ErbB-2/HER2-overexpressing tumors using combinations of monoclonal antibodies: relevance of receptor endocytosis." (2009) Proc Natl Acad Sci USA 106:3294-99.
Binder DC, Engels B, Arina A, Yu P, Slauch JM, Fu YX, et al. Antigen-specific bacterial vaccine combined with anti-PD-L1 rescues dysfunctional endogenous T cells to reject long-established cancer. Cancer immunology research. 2013;1(2):123-33.
Blattman, JN et al. "Cancerimmunotherapy: a treatment for the masses." (2004) Science 305:200-5.
Cai Z, Zhang H, Liu J, Berezov A, Murali R, Wang Q, et al. Targeting erbB receptors. Seminars in cell & developmental biology. 2010;21(9):961-6.
Campbell, MR et al. "HER3 comes of age: new insights into its functions and role in signaling, tumor biology, and cancer therapy." Clin cancer Res (2010) 16:1373-83.
Clay, T. et al., "Polyclonal Immune Responses To Antigens Associated With Cancer Signaling Pathways And New Strategies To Enhance Cancer Vaccines" (2011) Immunolo Res 49(0): 235-247.
Drake, CG et al. Mechanisms of immune evasion by tumors. (2006) Adv Immunol 90:51-81.
Dranoff, G. "Cytokines in cancer pathogenesis and cancer therapy." (2004) Nat Rev Cancer 4:11-22.
Eager, R et al. "GM-CSFF gene-transduced tumor vaccines." (2005) Mol Ther. 12:18-27.
Erjala, K et al. "Signaling via ErbB2 and ErbB3 associates with resistance and epidermal growth factor receptor (EGFR) amplication with sensitivity to EGRF inhibitor gefitnib in head and neck squamous cell carcinoma cells." (2006) Clin Cancer Res 12:4103-11.
Folgiero V, Avetrani P, Bon G, Di Carlo SE, Fabi A, Nistico C, et al. Induction of ErbB-3 expression by alpha6beta4 integrin contributes to tamoxifen resistance in ERbeta1-negative breast carcinomas. PLoS One. 2008;3(2):e1592.
Fourcade J, Sun Z, Pagliano O, Chauvin JM, Sander C, Janjic B, et al. PD-1 and Tim-3 regulate the expansion of tumor antigen-specific CD8(+) T cells induced by melanoma vaccines. Cancer Res. 2014;74(4):1045-55.
Frogne, T et al. "Activation of ErbB3, EGRF and Erk is essential for growth of human breast cancer cell lines with acquired resistance to fulvestrant." (2009) Breast Cancer Res Treat 114:263-75.

Friedman, LM et al. "Synergistic down-regulation of receptor tyrosine kinase by combinations of mAbs: implications for cancer immunotherapy." (2005) Proc Natl Acad Sci USA 102:1915-20.
Fu, J. et al., "Preclinical evidence that PD1 blockade cooperates with cancer vaccine TEGVAX to elicit regression of established tumors" (2014) Cancer Res, 74(15): 4042-4052.
Gala K, Chandarlapaty S. Molecular pathways: HER3 targeted therapy. Clin Cancer Res. 2014;20(6):1410-6.
Gallo, P. et al., "Xenogenic Immunization in Mice Using HER2 DNA Delivered by an Adenoviral Vector" (2005) Int. J. Cancer 113(1): 67-77.
Giltnane JM, Moeder CB, Camp RL, Rimm DL. Quantitative multiplexed analysis of ErbB family coexpression for primary breast cancer prognosis in a large retrospective cohort. Cancer. 2009;115(11):2400-9.
Goldman, B et al. "The cancer vaccine roller coaster." (2009) Nat Biotechnol 27:129-39.
Greenspan, N.S. et al., "Defining epitopes: It's not as easy as it seems," (1999) Nature Biotechnology 7:936-937.
Grupp et al., Chimeric antigen receptor-modified T cells for acute lymphoid leukemia. New England J. Med. 368:1509-18, (2013).
Hartman, Z. et al., "An Adenoviral vaccine encoding full-length inactivated human Her2 exhibits potent immunogenicity and enhanced therapeutic efficacy without oncogenicity" (2010) Clin Cancer Res 16(5): 1466-1477.
Hartman, Z. et al., "Ligand-independent TLR signals generated by ectopic overexpression of MyD88 generate local and systemic anti-tumor immunity" (2010) Cancer Res 70(18): 7209-7220.
Hartman, Z. et al., "Growth of triple-negative breast cancer cells relies upon coordinate autocrine expression of the proinflammatory cytokines IL-6 and IL-8" (2013) Cancer Res 73(11): 3470-3480.
Hartman, Z. et al., Increasing vaccine potency through exosome antigen targeting. Vaccine. Nov. 21, 2011;29(50):9361-7.
Hayashi M, Inokuchi M, Takagi Y, Yamada H, Kojima K, Kumagai J, et al. High expression of HER3 is associated with a decreased survival in gastric cancer. Clin Cancer Res. 2008;14(23):7843-9.
He, TC et al. "A simplified system for generating recombinant adenoviruses." (1998) Proc Natl Acad Sci USA 95:2509-14.
Hodges, BL et al. "Adenovirus vectors with the 100K gene deleted and their potential for multiple gene therapy applications." (2001) J Virol 75:5913-20.
Holbro, T et al. "The ErbB2/ErbB3 heterodimer functions as an oncogenic unti: ErbB2 requires ErbB3 to drive breast tumer cell proliferation." (2003) Proc Natl Acad Sci USA 100:8933-8.
Holmes, E.H., "PSMA specific antibodies and their diagnostic and therapeutic use," (2001) Exp. Opin. Invest. Drugs 10(3):511-519.
Hsieh AC, Moasser MM. Targeting HER proteins in cancer therapy and the role of the non-target HER3. Br J Cancer. 2007;97(4):453-7.
Huang, X et al. "Heterotrimerization of the growth factor receptors erbB2, erbB3, and insulin-like growth facotr-I receptor in breast cancer cells resistant to herception." (2010) Cancer Res 70:1204-14.
Junttila TT, Akita RW, Parsons K, Fields C, Lewis Phillips GD, Friedman LS, et al. Ligand-independent HER2/HER3/PI3K complex is disrupted by trastuzumab and is effectively inhibited by the PI3K inhibitor GDC-0941. Cancer Cell. 2009;15(5):429-40.
Karyampudi L, Lamichhane P, Scheid AD, Kalli KR, Shreeder B, Krempski JW, et al. Accumulation of memory precursor CD8 T cells in regressing tumors following combination therapy with vaccine and anti-PD-1 antibody. Cancer Res. 2014;74(11):2974-85.
Kennecke, H. et al., "Metastatic behavior of breast cancer subtypes" (2010) J Oncol 28(20): 3271-3277.
Kershaw, M.H. et al., "Gene-engineered T cells as a superior adjuvant therapy for metastatic cancer" (2004) J Immunol 173(3): 2143-2150.
Kol A, Terwisscha van Scheltinga AG, Timmer-Bosscha H, Lamberts LE, Bensch F, de Vries EG, et al. HER3, serious partner in crime: therapeutic approaches and potential biomarkers for effect of HER3-targeting. Pharmacol Ther. 2014;143(1):1-11.
Laheru, DA eta l. "Genes to vaccines for immunotherapy: how the molecular biology revolution has influenced cancer immunology." (2005) Mol Cancer Ther 4:1645-52.
Lee CH, Huntsman DG, Cheang MC, Parker RL, Brown L, Hoskins P, et al. Assessment of Her-1, Her-2, And Her-3 expression and

(56) References Cited

OTHER PUBLICATIONS

Her-2 amplification in advanced stage ovarian carcinoma. Int J Gynecol Pathol. 2005;24(2):147-52.
Lee-Hoeflich, ST et al. "A central role for HER3 in HER2-amplified breast cancer: implications for targeted therapy." (2008) Cancer Res 68:5878-87.
Leonard, JP et al. "Effects of single-dose interleukin-12 exposure on interleukin-12-associated toxicity and interferon-y production." (1997) Blood 90:2541-8.
Li B, VanRoey M, Wang C, Chen TH, Korman A, Jooss K. Anti-programmed death-1 synergizes with granulocyte macrophage colony-stimulating factor—secreting tumor cell immunotherapy providing therapeutic benefit to mice with established tumors. Clin Cancer Res. 2009;15(5):1623-34.
Liu, B et al. Downregulation of erbB3 abrogates erbB2-mediated tamoxifen resistance in breast cancer cells. (2007) Int J Cancer 120:1874-82.
Luo, et al. "A protocol for rapid generation of recombinant adenoviruses using the AdEasy system" (2007) Nature Protocols 2:1236.
Makhija, S et al. "clinical activity of gemcitabine plus pertuzumab in platinum-resistant ovarian cancer, fallopian tube cancer, or primary peritoneal cancer." (2010) J Clin Oncol 28:1215-23.
Miller, TW et al. "Loss of Phosphatase and Tensin homologue deleted on chromosome 10 enages ErbB3 and insulin-like growth factor-I receptor signaling to promote antiestrogen resistance in breast cancer." (2009) Cancer Res 69:4192-201.
Morse, MA et al. Synergism from combined immunologic and pharmacologic inhibition of HER2 in vivo. (2010) Int J Cancer 126:2893-903.
Musgrove EA, Sutherland RL. Biological determinants of endocrine resistance in breast cancer. Nat Rev Cancer. 2009;9(9):631-43.
Nabholtz, J.M. et al., "Anastrozole is superior to tamoxifen as first-line therapy for advanced breast cancer in postmenopausal women: results of a North American multicenter randomized trial. Arimidex Study Group" (2000) J Clin Oncol 18(22): 3758-3767.
Nanda R, Chow LQ, Dees EC, Berger R, Gupta S, Geva R, et al. Pembrolizumab in Patients With Advanced Triple-Negative Breast Cancer: Phase Ib KEYNOTE-012 Study. J Clin Oncol. 2016;34(21):2460-7.
O'Neil, LA et al. "Therapeutic targeting of toll-like receptors for infectious and inflammatory diseases and cnacer." (2009) Pharmacol Rev 61:177-97.
Ono, Y. et al., "Phorbol ester binding to protein kinase C requires a cysteine-rich zinc-finger-like sequence" (1989) Proc. Natl. Acad. Sci. USA 86:4856-4871.
Osada, T et al. "Vaccination targeting human HER3 alters the phenotype of infiltrating T cells and respones to immune checkpoint inhibition." (2017). OncoImmunology 0(0).
Osada T, Yang XY, Hartman ZC, Glass O, Hodges BL, Niedzwiecki D, et al. Optimization of vaccine responses with an E1, E2b and E3-deleted Ad5 vector circumvents pre-existing anti-vector immunity. Cancer Gene Ther. 2009;16(9):673-82.
Osipo, C eta l. "Role for HER2/neu and HER3 in fulvestrant-resistant breast cancer." (2007) Int J Oncol 30:509-20.
Pederson, MW et al. "Sym004: a novel synergistic anti-epidermal growth factor receptor antibody mixture with superior anticancer efficacy." (2010) Cancer Res 70:588-97.
Prigent, SA et al. "Identification of c-erbB-3 binding sites for phosphatidylinositol 3'-kinase and SHC using an EGF receptor/c-erbB-3 chimera." (1994) Embo J 13:2831-41.
Pulaski, BA et al. "Reduction of established spontaneous mammary carcinoma metastases following immunotherapy with major histocompatibility complex class II and B7.1 cell-based tumor vaccines." (1998) Cancer Res. 58:1486-93.
Renard, V. et al., "HER-2 DNA and Protein Vaccines Containing Potent Th Cell Epitopes Induce Distinct Protective and Therapeutic Antitumor Responses in HER-2 Transgenic Mice" (2003) J Immunol 171(3): 1588-1595.

Ren et al. "Polyclonal Her2-specific antibodies induced by vaccination mediate receptor internalization and degradation in tumor cells" (2012) Breast cancer research 14: R89.
Reschke M, Mihic-Probst D, van der Horst EH, Knyazev P, Wild PJ, Hutterer M, et al. HER3 is a determinant for poor prognosis in melanoma. Clin Cancer Res. 2008;14(16):5188-97.
Rosenberg, SA et al., Adoptive cell transfer: a clinical path to effective cancer immunotherapy. Nat. Rev. Cancer 8 (4): 299-308 (2008).
Sakai K, Yokote H, Murakami-Murofushi K, Tamura T, Saijo N, Nishio K. Pertuzumab, a novel HER dimerization inhibitor, inhibits the growth of human lung cancer cells mediated by the HER3 signaling pathway. Cancer Sci. 2007;98(9):1498-503.
Schoeberl, Birgit et al. "An ErbB3 Antibody, MM-121, Is Active in Cancers with Ligand-Dependent Activation" (2010) Cancer Research: 70(6): 2485-2494.
Sergina, NV et al. "Escape from HER-family tyrosine kinase inhibitor therapy by the kinase-inactive HER3." (2007) Nature 445:437-41.
Soares KC, Rucki AA, Wu AA, Olino K, Xiao Q, Chai Y, et al. PD-1/PD-L1 blockade together with vaccine therapy facilitates effector T-cell infiltration into pancreatic tumors. J Immunother. 2015;38(1):1-11.
Soltoff, SP et al. "ErbB3 is involved in activation of phosphatidylinositol 3-kinase by epidermal growth factor." (1994) Mol Cell Biol 14:3550-3558.
Takikita M, Xie R, Chung JY, Cho H, Ylaya K, Hong SM, et al. Membranous expression of Her3 is associated with a decreased survival in head and neck squamous cell carcinoma. J Transl Med. 2011;9:126.
Tanaka, T. et al., "Efficient generation of antibodies to oncoproteins by using synthetic peptide antigens," (1985) Proc. Natl. Acad. Sci. USA 82:3400-3404.
Tiriveedhi V, Tucker N, Herndon J, Li L, Sturmoski M, Ellis M, Ma C, Naughton M, Lockhart AC, Gao F, et al. Safety and preliminary evidence of biologic efficacy of a mammaglobin—a DNA vaccine in patients with stable metastatic breast cancer. Clinical cancer research : an official journal of the American Association for Cancer Research. 2014;20(23):5964-75.
Topalian SL, Drake CG, Pardoll DM. Immune checkpoint blockade: a common denominator approach to cancer therapy. Cancer Cell. 2015;27(4):450-61.
Tovey S, Dunne B, Witton CJ, Forsyth A, Cooke TG, Bartlett JM. Can molecular markers predict when to implement treatment with aromatase inhibitors in invasive breast cancer? Clin Cancer Res. 2005;11(13):4835-42.
Van Elsas A, Hurwitz AA, Allison JP. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. 1999;190(3):355-66.
Xia W, Petricoin EF, 3rd, Zhao S, Liu L, Osada T, Cheng Q, et al. An heregulin-EGFR-HER3 autocrine signaling axis can mediate acquired lapatinib resistance in HER2+ breast cancer models. Breast cancer research : BCR. 2013;15(5):R85.
Yoo, J.Y. et al., "Downregulation of ErbB3 Expression by Adenovirus Expressing ErbB3 Specific shRNA Enhances Antitumor Efficacy through Apoptosis Induction" (2009) Molecular Therapy: 17(Suppl. 1): S106.
Yuan, J. et al., "CTLA-4 blockade increases antigen-specific CD8(+) T cells in prevaccinated patients with melanoma: three cases" (2011) Cancer Immunol Immunother, 60(8): 1137-1146.
Yu, P et al. "Targeting the primary tumor to generate CTL for the effective eradication of spontaneous metastases." (2007) J Immunol 179:1960-8.
Zhang, Y et al. "EBPI, an ErbB3-binding protein, is decreased in prostate cancer and implicated in hormone resistance." (2008) Mol Cnacer Ther 7:3176-86.
Zitvogel, L et al. "The anticancer immune response: indispensable for therapeutic success?" (2008) 118:1991-2001.
International Search Report and Written Opinion for PCT/US2013/022396 dated May 3, 2013 (13 pages).

(56) References Cited

OTHER PUBLICATIONS

Office Action for U.S. Appl. No. 14/373,103 dated Oct. 26, 2015 (17 pages).
Office Action for U.S. Appl. No. 14/373,103 dated Apr. 27, 2016 (20 pages).
Office Action for U.S. Appl. No. 14/373,103 dated Sep. 23, 2016 (12 pages).
Office Action for U.S. Appl. No. 14/373,103 dated Sep. 1, 2017 (7 pages).

* cited by examiner

Fig. 1D

| HER3-VIA Antibody epitopes | |
|---|---|
| Epitope(s) position | Protein region |
| 101-111 | ECD |
| 153-167 | ECD |
| 185-191 | ECD |
| 209-223 | ECD |
| 369-375 | ECD |
| 501-511 | ECD |
| 589-599 | ECD |
| 649-663 | TM |
| 681-691 | ICD |
| 865-875 | ICD |
| 881-895 | ICD |
| 901-915 | ICD |
| 981-988 | ICD |
| 1037-1051 | ICD |
| 1105-1119 | ICD |
| 1153-1163 | ICD |
| 1249-1255 | ICD |
| 1268-1279 | ICD |

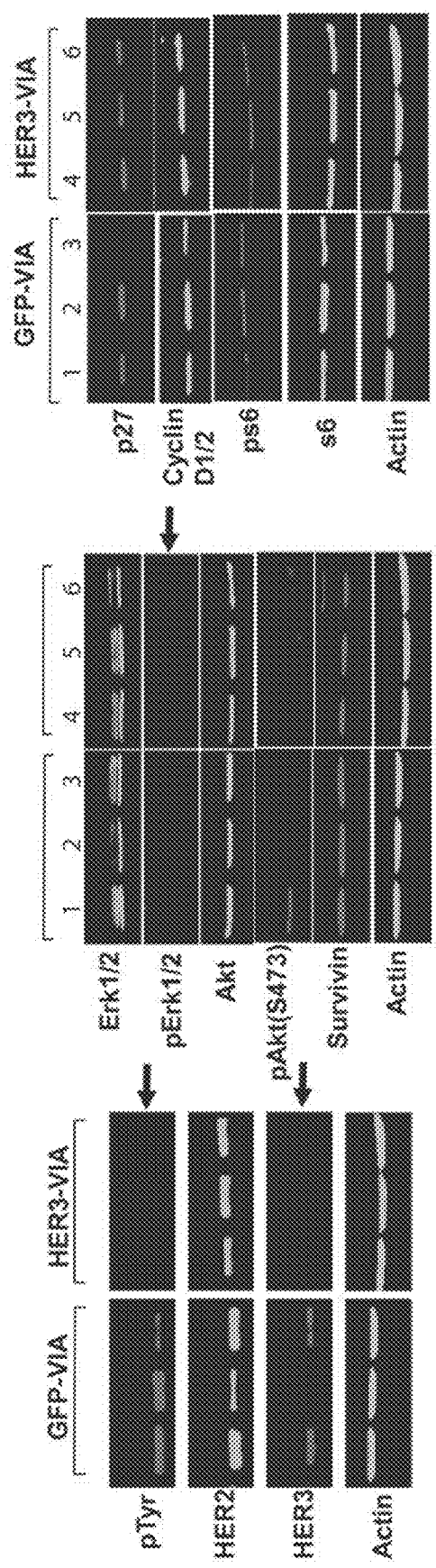

VACCINES AGAINST ANTIGENS INVOLVED IN THERAPY RESISTANCE AND METHODS OF USING SAME

CROSS-REFERENCE TO RELATED APPLICATIONS

This patent application is a continuation of U.S. patent application Ser. No. 14/373,103, filed Jul. 18, 2014, now issued as U.S. Pat. No. 9,956,276 on May 1, 2018, which is a national stage filing under 35 U.S.C. 371 of International Application No. PCT/US2013/022396, filed Jan. 21, 2013, which claims the benefit of priority of U.S. Provisional Patent Application No. 61/588,449, filed Jan. 19, 2012, both of which are incorporated herein by reference in their entirety.

STATEMENT REGARDING FEDERALLY SPONSORED RESEARCH

This invention was made with United States government support awarded by the National Cancer Institute grant numbers P50 CA89496-01, P50 CA068438 and R01 CA95447 and by Department of Defense grant number BC050221. The United States has certain rights in this invention.

SEQUENCE LISTING

This application was filed electronically via EFS-Web and includes an electronically submitted Sequence Listing in .txt format. The .txt file contains a sequence listing entitled "2013-01-21_5667-00104_Sequence_Listing_as_Filed" created on Jan. 21, 2013 and is 64.7 kilobytes in size. The Sequence Listing contained in this .txt file is part of the specification and is hereby incorporated by reference herein in its entirety.

INTRODUCTION

This application relates to a cancer vaccine, specifically a vaccine against antigens that are expressed in response to resistance to therapeutic intervention to cancer (or pre-cancers), with a proof of principle antigen, HER3, as an example. Methods of using the vaccines and methods of developing vaccines capable of blocking the development of resistance to cancer therapies are also provided.

Cancer vaccines target antigens expressed by tumors, but application of these vaccines has not been as effective as once hoped due to induction of immune tolerance by chronic overexpression of the targeted protein in the absence of co-stimulatory molecules and the induction of an immuno-modulatory environment. Preventative cancer vaccines may be more promising, but cancers are highly variable, with multiple genetic changes, but few truly universal changes. Thus, it is difficult to predict what antigens will be overexpressed on any specific cancer or whether an individual should be vaccinated and if so, with what antigens. In contrast, a strategy is proposed here in which vaccination against the antigen(s) that will predictably be overexpressed in response to a therapy, but prior to that antigen's overexpression by the cancer cells is used to induce a robust anti-cancer immune response.

SUMMARY

Provided herein is a mechanism of revolutionizing cancer therapy or prevention by preventing the development of resistance to cancer therapeutic or cancer prevention agents by identifying which antigens are likely to be expressed in a cancer or precancer in response to treatment with a cancer therapeutic or prevention agent and thus which antigens may be targeted with a vaccine in patients. Also provided is a vaccine targeting a specific antigen involved in a resistance mechanism, namely HER3, and methods of using the vaccine. In one aspect, the vaccine includes a polynucleotide encoding a HER3 polypeptide. For example, a HER3 polypeptide of SEQ ID NO: 1 or 2 may be included in a vaccine.

In another aspect, methods of treating a cancer or precancer or reducing the likelihood of the cancer or precancer to develop resistance to a cancer therapeutic or prevention agent by administering the vaccine provided herein to a subject with cancer or precancer are provided. The vaccine may be administered before, concurrently with or after administration of the cancer therapeutic or prevention agent.

In yet another aspect, methods of reducing the likelihood of a cancer or precancer developing resistance to a cancer therapeutic or prevention agent by administering the cancer therapeutic or prevention agent and a vaccine to the subject are provided. The vaccine includes a polynucleotide encoding a polypeptide whose expression or activation correlates with development of resistance of the cancer or precancer to the cancer therapeutic or prevention agent. Co-administration of the cancer therapeutic or prevention agent and the vaccine inhibits the generation of resistance to the cancer therapeutic or prevention agent and increases the therapeutic potential of the cancer therapeutic agent and the prevention potential of the cancer prevention agent.

BRIEF DESCRIPTION OF THE DRAWINGS

FIG. 1A-1D is a set of figures showing HER3 specific T cell and B cell responses to Ad-HER3 in vivo. FIG. 1A is a graph showing the number of IFN-γ secreting splenocytes by ELISPOT after 6-8 week old BALB/c mice were immunized once with $2.6 \times 10^{10}$ Ad-HER3 or Ad-GFP via bilateral subcutaneous footpad injections. Two weeks following the vaccination mice were euthanized and splenocytes collected for analysis in an Interferon-gamma ELISPOT assay. Splenocytes from Ad-HER3 vaccinated and not or Ad-GFP vaccinated (control) mice recognized HER3 intracellular domain (ICD) and extracellular domain (ECD) peptide libraries and the mixture of both libraries (Mix) in interferon-gamma ELISPOT assays. The mean from 5 mice per group is shown with error bars denoting standard deviation. CT−; splenocytes alone. CT+; Splenocytes plus PMA (50 ng/mL) and Ionomycin (1 ng/mL) as a control for the assay. FIG. 1B is a set of FACS analysis histograms of peripheral blood serum from the mice was tested for the presence of antibodies capable of binding to tumor cell-expressed HER3. Flow cytometric analysis was used and histograms denote binding of HER3-vaccine induced antibodies (HER3-VIA) in serum to human breast cancer cell line BT474. FIG. 1C is a graph showing the mean fluorescence intensity which was calculated for the binding of HER3-VIA against a panel of human breast cancer cell lines with dilutions of the serum. FIG. 1D shows the results of epitope mapping of HER3-VIA using spotted 15mer peptide arrays and revealed recognition of 18 different epitopes.

FIG. 2A is a set of graphs showing that HER-3 VIA mediate complement dependent cytotoxicity (CDC) against HER3-expressing (BT474, T47D, MDA-MB-468, BT474M1) human breast cancer cell lines but not against the HER3-negative cell line (MDA-MB-231). Black bars, HER3-VIA; white bars, GFP-VIA; grey bars, Trastuzumab. Trastuzumab does not mediate CDC. FIG. 2B is a graph showing that HER-3 VIA mediate antiproliferative activity against HER3-expressing (BT474, T47D, MDA-MB-468, BT474M1) human breast cancer cell lines but not against the HER3-negative cell line (MDA-MB-231) in a 72 hour assay. The antiproliferative effect implied receptor modulation and FIG. 2C is a set of photographs showing that binding of HER3-VIA results in rapid internalization of endogenous HER3 receptor expressed on the surface of human breast cancer cell lines.

FIG. 3A-3D is a set of figures showing the in vivo effects of HER3-VIA on BT474M1 human breast tumor xenografts. FIG. 3A is a cartoon showing the experiment schema. HER3-VIA or control GFP-VIA were transferred via tail vein injections. FIG. 3B is a graph showing that HER3-VIA retarded the growth of established BT474M1 breast cancers (p<0.005 at *). FIG. 3C is a set of photographs showing immunohistochemistry analysis of HER3 protein expression in excised tumors and revealed a dramatic loss of HER3 protein in the HER3-VIA-treated mice compared to GFP-VIA treated mice. GFP-VIA-treated mouse tumors retained HER3 protein levels seen in tumors from mice "treated" with saline. FIG. 3D is a set of photographs of Western blot analysis of excised tumors for expression of the indicated proteins.

FIG. 4A is a graph showing that passive transfer of HER3-VIA retarded the growth of established lapatinib-refractory BT474 tumors in SCID mice demonstrating that anti-HER3 immunity can treat therapy resistant tumors (p<0.025 at *). FIG. 4B is a set of photographs showing Western blot analysis of excised tumors to perform pathway analysis. FIG. 4C is a set of photographs showing immunohistochemical analysis of excised tumors and revealed no significant change in HER3 levels compared to controls.

DETAILED DESCRIPTION

Figure 1A:
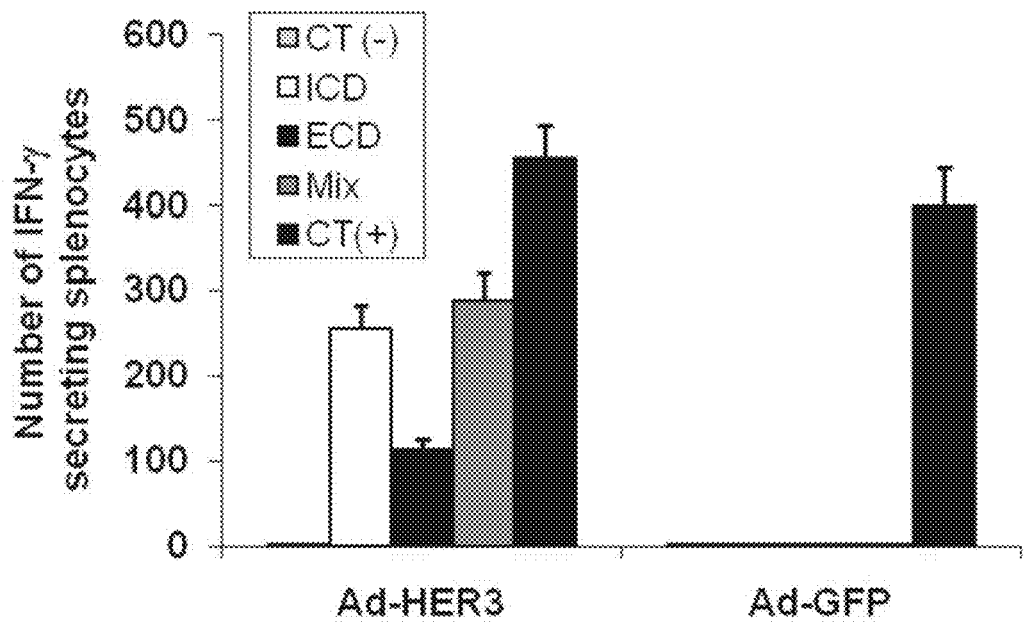

As a novel alternative to vaccines targeting well established tumor antigens, we hypothesized that the antigen-specific immune non-responsiveness to conventional tumor-associated antigens may be avoided by targeting tumor antigens that are induced after exposure to a cancer therapeutic or prevention agent as a mechanism of developing therapeutic resistance. Although there may be many potential antigens overexpressed in response to a cancer therapeutic or prevention agent, those antigens that are likely critical components of specific therapeutic resistance mechanisms would be attractive targets, as immunologic ablation of clones expressing such antigens should eliminate the clinical recurrence of therapy resistant tumor cells. One such antigen thought to be essential to therapeutic resistance is a member of the HER family of receptor tyrosine kinases (RTKs), and to endocrine therapies, HER3.

HER3, although lacking catalytic kinase activity, is thought to function as a signaling substrate for other HER proteins with which it heterodimerizes. Although not transforming by itself, HER3 has tumor promoting functions in some cancers, including a role as a co-receptor for amplified HER2 with which it is synergistically co-transforming and rate-limiting for transformed growth. Treatment of HER2-amplified breast cancers with HER2-targeting tyrosine kinase inhibitors (TKIs) leads to an increase in HER3 expression and downstream signaling that results in therapeutic resistance.

The pivotal role of HER3 as a hub for HER family signaling has made it an attractive therapeutic target, but its' lack of kinase activity prevents small molecule HER3 specific TKIs from being generated. Nonetheless, HER3 may be targeted with antibodies which have diverse functional consequences depending on their binding site. For example, the anti-HER2 monoclonal antibody pertuzumab disrupts neu-regulin-induced HER2-HER3 dimerization and signaling; however, it is less effective at disrupting the elevated basal state of ligand-independent HER2-HER3 interaction and signaling in HER2-overexpressing tumor cells. Other HER3-specific antibodies under development bind to, and cause internalization of, HER3, inhibiting downstream signaling. As an alternative to monoclonal antibodies, we have recently demonstrated that polyclonal antibodies induced by vaccination against receptors such as HER2 can mediate profound receptor internalization and degradation, providing a therapeutic effect in vitro and in vivo (Ren et al., Breast cancer Research 2012 14: R89).

Therefore, we generated a recombinant adenoviral vector expressing human HER3 (Ad-HER3) and demonstrated that it elicited HER3 specific B and T cell immune responses as shown in the Examples. Furthermore, we demonstrated that HER3 specific antibodies recognized multiple HER3 epitopes, bound to tumor membrane expressed HER3, mediated complement dependent lysis and altered downstream signaling mediated by receptor heterodimers involving HER3. In addition, we found that HER3 specific polyclonal antisera had specific activity in mediating HER3 internalization and degradation. Finally, we demonstrated that HER3 specific polyclonal antisera was well tolerated when transferred to tumor bearing animals, yet retarded tumor growth in vivo, including retarding the growth of HER2 therapy-resistant tumors. These data suggest that Ad-HER3 is an effective vaccine which should be tested for therapeutic efficacy in clinical trials targeting cancers that overexpress HER3 in response to a targeted therapy. The general application of this vaccination strategy can be applied to other antigens expressed in HER therapy resistant tumors, as well as antigens induced by other resistance mechanisms, and represents a new conceptual framework for cancer immunotherapy.

As described in the appended examples, generation of resistance to cancer therapeutic or prevention agents is a common problem in the treatment of cancer or precancer and in several cases the mechanism of resistance to the therapeutic agent is known. Resistance is often the result of changes in gene expression (over-expression or blocked expression of a protein), change in the gene by mutation, or altered sequences by altered splicing or translocation or altered activation of a protein in the cells (over-activation or blocked activation of a protein).

In those cases where over-expression or over-activation of a protein, or a new sequence in the protein is responsible for increasing the resistance of the cancer or precancer cells to the therapeutic or prevention agent, we report a method for reducing the likelihood that the cancer or precancer will develop resistance to the cancer therapeutic or prevention agent. As used herein, resistance to a cancer therapeutic or prevention agent indicates that the cancer therapeutic or prevention agent is not as effective at inhibiting the growth of, or killing, cancer or precancer cells in response to the cancer therapeutic or prevention agent. The method may even block the development of resistance to the cancer therapeutic or prevention agent or may reverse resistance to the cancer therapeutic or prevention agent after it has developed. The methods include administering the cancer therapeutic or prevention agent and administering a vaccine to the subject in need of treatment for a cancer. The vaccine comprises a polynucleotide encoding a polypeptide whose expression or activation is correlated with or results in development of resistance of the cancer or precancer to the cancer therapeutic or prevention agent.

The vaccine may be administered before, during or after treatment with the cancer therapeutic or prevention agent or may be administered simultaneously with the cancer therapeutic or prevention agent. The administration of the vaccine and the cancer therapeutic or prevention agent to the subject reduces the likelihood that the subject's cancer or precancer will develop resistance to the therapeutic or prevention agent as compared to a control subject with a similar cancer or precancer not administered the vaccine or as compared to the general likelihood of a population of subjects having the cancer or precancer. In some embodiments, the cancer or precancer in individuals administered both the vaccine and the therapeutic or prevention agent does not develop resistance to the cancer therapeutic or prevention agent and is treated. Alternatively, the growth of the cancer or precancer may be inhibited or the growth rate reduced. The administration of the vaccine and cancer therapeutic or prevention agent may also reverse resistance to the cancer therapeutic or prevention agent if the cancer or precancer is already resistant to the cancer therapeutic or prevention agent. In some embodiments, administration of the vaccine is sufficient to treat the cancer or inhibit the growth or kill the cancer. In other embodiments, the vaccine must be administered in conjunction with the cancer therapeutic or prevention agent or prior to development of resistance to the cancer therapeutic or prevention agent by the cancer.

The vaccine may include a polynucleotide encoding a HER3 polypeptide. The mature HER3 protein sequence is provided in SEQ ID NO: 1 and the complete HER3 protein precursor sequence is provided in SEQ ID NO: 2. Polynucleotide sequences for HER3 are provided in SEQ ID NO:3 (mRNA) and SEQ ID NO: 4 (DNA). The vaccine may comprise full-length HER3 or portions thereof. For example, the vaccine may comprise only the extracellular domain or the extracellular domain plus the transmembrane domain or other portions of the HER3 polypeptide. Suitably the vaccine is capable of eliciting an immune response to HER3 in a subject administered the vaccine. The immune response may be a B cell or T cell response. Suitably the immune response includes an antibody response directed to HER3. The immune response may be a polyclonal antibody response in which multiple epitopes of HER3 are recognized by antibodies.

As reported in the examples, in a mouse model a HER3 vaccine was able to generate a robust polyclonal antibody response to HER3 and several epitopes were identified. See FIG. 1D. The epitopes identified in FIG. 1D include the polypeptides identified in SEQ ID NOs: 5-22, which represents portions of SEQ ID NO:2. It is expected that some of these epitopes may be immunogenic in humans as well. Those of skill in the art will appreciate that a vaccine including polynucleotides encoding only portions of full-length HER3, i.e. antigenic epitopes, may be used in the vaccines described herein.

The vaccine may include a vaccine vector. The vaccine vector may be a bacterial, yeast, viral or liposomal vaccine vector. The vaccine may be a DNA vaccine as well and not include a vaccine vector. The vaccine vector may be an adenovirus or adeno-associated virus. In the Examples an adenovirus was used as the vaccine vector. The vaccine vector may contain the HER3 polynucleotide or portions thereof. The vaccine vector may contain the HER3 polypeptide or portions thereof. The vaccine vector may express the HER3 polypeptide or portions thereof. HER3 polypeptide or portions thereof may be expressed on the surface or interior of the vaccine vector. HER3 polynucleotide or portions thereof may be carried within the vaccine vector and the HER3 polypeptide or portions thereof may be expressed only after vaccination. HER3 polypeptides or portions thereof may be expressed as a fusion protein or in conjunction with adjuvants or other immunostimulatory molecules to further enhance the immune response to the polypeptide.

Methods of treating a cancer or precancer, or of reducing the likelihood of the cancer or precancer developing resistance to a cancer therapeutic or prevention agent, are also provided. The methods include administering the vaccine as described above to a subject having cancer or precancer. The subject may be any mammal, suitably a human, domesticated animal such as a dog or cat, or a mouse or rat. A cancer therapeutic or prevention agent may be administered concurrently with, before or after administration of the vaccine.

The cancer therapeutic or prevention agents may be any agent capable of treating the cancer or inhibiting growth of cancer cells. Suitable agents include those which target HER2, HER1/EGFR, estrogen receptor or IGF1R. The therapeutic agent may be trastuzumab, lapatinib, pertuzumab or another HER2 targeting therapeutic agent or it may be an EGFR targeting therapeutic agent such as cetuximab or erlotinib, or it may be an antiestrogen, or an agent that prevents estrogen synthesis such as an aromatase inhibitor. In particular, the Examples demonstrate that a HER3 vaccine can treat a HER2 positive cancer when used in combination with a therapeutic agent targeting HER2. Cancer cells often develop resistance to HER2 targeting therapeutic agents. Addition of vaccination with a HER3 vaccine or passively transferred polyclonal antibodies specific for HER3 resulted in blocking resistance, inhibited cancer cell growth and resulted in treatment of the cancer.

Suitably the vaccinated subject develops an immune response to HER3 in response to administration of the vaccine. The immune response may be an antibody or T cell immune response. For example the immune response may include antibody-dependent cellular cytotoxicity, polyclonal antibody response, complement dependent cellular cytotoxicity, cellular cytotoxicity, disruption of ligand binding, disruption of dimerization, mimicking ligand binding causing internalization of HER3, or degradation of HER3. The immune response may comprise an antibody response directed to at least one of SEQ ID NOs: 5-22. As shown in the Examples, transfer of HER3 specific antibodies was sufficient to treat the cancer and inhibit the development of resistance to the therapeutic agent.

Reduction of the development of resistance can be measured in several ways. The resistance of the vaccinated subject may be compared to a similar subject that was not vaccinated as in the Examples. Alternatively, the reduction may be measured based on statistics generated regarding the likelihood of an individual being treated with the therapeutic agent to develop resistance versus that of individuals treated with the therapeutic agent and vaccinated with HER3. The reduction in the likelihood of resistance of the cancer may also be measured by measuring the level of HER3 expression on the surface of cancer cells. HER3 expression is reduced on cancer cells after effective administration of the vaccine. The effectiveness of the vaccine in treating the cancer or reducing the likelihood of resistance can be measured by tracking the growth of the tumor or the growth rate of the tumor or cancer cells. A decrease in tumor size or in the rate of tumor growth is indicative of treatment of the cancer.

The cancer may be selected from any cancer capable of developing resistance to a therapeutic agent by increasing expression or activation of a protein by the cancer cells. In particular the cancer may be any cancer capable of developing resistance to a therapeutic agent which targets a HER family tyrosine kinase, suitably HER2 or EGFR or the estrogen receptor, suitably anti-estrogens. The cancer may develop resistance by increasing the expression of HER3, which although not a kinase, will dimerize with another HER family kinase and allow for signaling to occur. Suitably the cancers are selected from breast, prostate, lung, ovarian, colon, rectal, pancreas, bladder, head and neck or liver cancers or precancers. The resistance may be due to a single or multiple changes, and the vaccine can target one or more of these changes, and/or include multiple antigens likely found in resistance cells, but not necessarily in all resistance cells.

Treating cancer includes, but is not limited to, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

Co-administration, or administration of more than one composition (i.e. a vaccine and a therapeutic agent) to a subject, indicates that the compositions may be administered in any order, at the same time or as part of a unitary composition. The two compositions may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

An effective amount or a therapeutically effective amount as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions (i.e. the vaccines and the therapeutic agents) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or transmucosal absorption. Thus the compositions may be formulated as an ingestable, injectable, topical or suppository formulation. The compositions may also be delivered with in a liposomal or time-release vehicle. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce the growth of the cancer at least 10%, 20%, 30%, 40%, 50%, 60%, 70%, 80%, 90%, 100% or more as compared to no treatment or treatment with only the therapeutic agent. It is specifically contemplated that pharmaceutical preparations and compositions may palliate, block further growth or alleviate symptoms associated with the cancer without providing a cure, or, in some embodiments, may be used to cure the cancer and rid the subject of the disease.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The vaccine vector may be administered one time or more than one time to the subject to effectively boost the immune response against HER3. If the vaccine is provided as a vaccine vector, the vaccine vector may be administered based on the number of particles delivered to the subject (i.e. plaque forming units or colony forming units). The subject may be administered 1012, 1011, 1010, $10^9$, $10^8$, $10^7$ or $10^6$ particles.

The examples provided herein are meant only to be illustrative and are not meant as limitations on the scope of the invention or of the appended claims. All references cited herein are hereby incorporated by reference in their entireties.

EXAMPLES

Materials and Methods
Cell Lines and Cell Culture Reagents.

The human breast cancer cell lines BT474, MDA-MB-231, MDA-11, 468, SKBR3, and T4 7D were obtained from the ATCC and grown in recommended media. The BT474M1 human breast tumor cell line was a gift from Dr. Mien-Chie Hung at The University of Texas M. D. Anderson Cancer Center and was grown in DMEM/F12 with 10% FBS. Laptinib-resistant BT474 (rBT474) were generated as previously described. Xia et al. A model of acquired autoresistance to a potent ErbB2 tyrosine kinase inhibitor and a therapeutic strategy to prevent its onset in breast cancer. Proc Natl Acad Sci USA 2006; 103:7795-800. Trastuzumab (Herceptin™, Genentech, San Francisco, Calif.) was purchased from the Duke Pharmacy.
Adenovirus Vector Preparation.

The human HER3 cDNA was excised from a pCMVSport6-HER3-HsIMAGE6147464 plasmid (cDNA clone MGC:88033/IMAGE:6147464) from the ATCC (Manassas, Va.), and construction of first-generation [E1-, E3-] Ad vectors containing human full length HER3 under control of human CMV promoter/enhancer elements was performed using the pAdEasy system (Agilent technologies, Santa Clara, Calif.) as previously described. Morse et al. Synergism from combined immunologic and pharmacologic inhibition of HER2 in vivo. Int J Cancer 2010; 126:2893-903; Amalfitano et al. Production and characterization of improved adenovirus vectors with the E1, E2b, and E3 genes deleted. J Virol 1998; 72:926-33; Hartman et al. An adenoviral vaccine encoding full-length inactivated human Her2 exhibits potent immunogenicty and enhanced therapeutic efficacy without oncogenicity. Clin Cancer Res 2010; 16:1466-77; and He et al. A simplified system for generating recombinant adenoviruses. Proc Natl Acad Sci USA 1998; 95; 2509-14.
Mice.

BALB/c and NOD.CB17-Prkdc$^{scid}$/J mice were purchased from Jackson Labs (Bar Harbor, Me.). All work was conducted in accordance with Duke IACUC-approved protocols. Induction of VIA: BALB/c mice were vaccinated on day 0 and day 14 via footpad injection with Ad-GFP, or Ad-HER3 vectors ($2.6 \times 10^{10}$ particles/mouse). Fourteen days after the second vaccination, mice were euthanized and sera were collected and stored at −80° C.
MIT Assay to Detect Cell Proliferation.

The effect of VIA-HER3 on the proliferation of human breast cancer cell lines was measured as previously described. Morse et al. Synergism from combined immunologic and pharmacologic inhibition of HER2 in vivo. Int J Cancer 2010; 126:2893-903. Briefly, 5000 cells per well in a 96-well plate were cultured with HER3-VIA. (1:33 dilution) or control serum GAP-VIA. (1:33 dilution) or Trastuzumab 20 µg/ml for 3 days and proliferation was assessed by MTT assay.
Western Blotting to Analyze Pathway Inhibition.

Tumors were isolated from euthanized mice and immediately flash frozen. Tissue extracts were prepared by homogenization in RIPA buffer as previously described by Morse et al. 2010. Equal amounts of proteins (50 ug) were resolved by 4-15% gradient SDS PAGE After transfer membranes were probed with specific antibodies recognizing target proteins: pTyr (Sigma), ErbB2, ErbB3, Akt, pAkt473, Erk 1/2, pErk1/2, (Cell Signaling, Beverly, Mass.) survivin, and actin (Sigma, St. Louis, Mo.), 4EBP-1, p4EBP-1, s6, ps6 (Santa Cruz Biotech., Santa Cruz, Calif.) and IRDye 800 conjugated anti-rabbit or mouse IgG or Alexa Fluor 680 anti-rabbit IgG and were visualized using the Odyssey Infrared Imaging System (LI-COR, Lincoln, Nebr.).
ELISPOT Analysis.

IFN-gamma ELISPOT assays (Mabtech, Cincinnati, Ohio) performed as previously described by Morse et al, 2010. HER3 peptide mix (1 mcg/mL was used; Jerini Peptide Technologies, Berlin, Germany), HIVgag peptide mix (BD Bioscience), or a mixture of PMA (50 ng/mL) and Ionomycin (1 ng/mL) were used. Six replicate wells for each condition were scored using the KS ELISPOT Reader with the KS ELISPOT 4.9 Software (Carl Zeiss, Munchen-Hallbergmoos, Germany), reporting responses as the mean of the replicate 6 wells.
Analysis of Anti-HER3 Antibody Binding by Flow Cytometry.

We have adapted a methodology reported by Piechocki et al. to measure anti-HER3 vaccine induced antibodies in vaccinated mouse serum by flow cytometry. Hartman et al. An adenoviral vaccine encoding full-length inactivated human Her2 exhibits potent immunogenicty and enhanced therapeutic efficacy without oncogenicity. Clin Cancer Res 2010; 16:1466-77 and Piechocki et al. Quantitative measurement of anti-ErbB-2 antibody by flow cytometry and ELISA. J Immunol Methods 2002; 259:33-42. Briefly, $3 \times 10^5$ human breast cancer cells were incubated with diluted (1:100 to 1:51, 200) mouse serum antibodies (HER3-VIA or CFP-VIA) for 1 h at 4° C. and then washed with 1% BSA-PBS. The cells were further stained with PE-conjugated anti-mouse IgG (Dako, Cat #R0480) for 30 minutes at 4° C., and washed again. Samples were analyzed on a BD LSRII flow cytometer (Becton Dickenson, San Jose, Calif.) and mean fluorescence intensity (MFI) reported.
Complement Dependent Cytotoxicity Assay.

We performed complement dependent cytotoxicity assays using our previously published protocol in Morse et al. 2010. Briefly, target cells were incubated with rabbit serum (1:100) as a source of complement and the HER3-VIA or GFP-VIA in sera from mice immunized as above diluted (1:100), or Trastuzumab (20 mcg/ml) at 37° C. for 2 hrs.

After incubation, cytotoxicity was measured using the Cyto-Tox 96 Nonradioactive Cytotoxicity Assay (Promega; per manufacturer's instructions) to measure LDH release in the culture media as evidence of cytotoxicity.

Assessment of HER3 Internalization

Human HER3+ breast cancer cells (SKBR3 and BT474M1) were incubated with 1:100 HER3-VIA or GFP-VIA at 37° C. for 60 minutes. After washing, fixation with 4% PFA, and permeabilization with permeabilizing solution 2 (Becton Dickenson), nonspecific binding was blocked with 2.5% Goat Serum at 37° C. for 30 min. Cells were incubated with 1:100 Red™-conjugated anti-mouse IgG (H+L) (Jackson ImmunoResearch Laboratories Inc. West Grove, Pa.) in a dark chamber for 1 hour at room temperature and washed with PBS. Slides were mounted in VectaShield containing DAPI (Vector Laboratories, Burlingame, Calif.) and images acquired using a Zeiss Axio Observer widefield fluorescence microscope (Carl Zeiss, Mtinchen-Hallbergmoos, Germany).

Treatment of Established HER3+BT474M1 Human Tumor Xenografts by Passive Transfer of Vaccine Induced Antibodies.

Eight to 10 week old NOD.CB17-Prkdc$^{scid}$/J mice (Jackson Labs., Bar Harbor, Me.) were implanted in the back with 17 Beta-Estradiol pellets (0.72 mg 60 day continuous release pellets; Innovative Research of American, Sarasota, Fla.) two days prior to tumor implantation. Five million BT474M1 tumor cells in 50% Matrigel were injected into the mammary fat pad. Tumors were allowed to develop for 14 days and then mice were randomized to receive iv injection of either GFP-VIA or HER3-VIA (5 mice per group). 100-150 microliters of VIA was injected at 2-3 day intervals for a total of 10 administrations. Tumor growth was measured in two dimensions using calipers and tumor volume determined using the formula volume=1/2 [(width)× (length)].

Treatment of Established HER3+ Lapatinib-Resistant rBT474 Human Tumor Xenografts by Passive Transfer of Vaccine Induced Antibodies.

Eight to 10 week old NOD.CB17-Prkdc$^{scid}$/J mice (Jackson Labs., Bar Harbor, Me.) were implanted in the mammary fat pad with 1 million lapatinib-resistant rBT474 tumor cells in 50% Matrigel. Tumors were allowed to develop for two months and then mice were randomized to receive iv injection of either GFP-VIA or HER2-VIA (5 mice per group). 100-150 microliters of VIA was injected at 2-3 day intervals for a total of 10 administrations. Tumor growth was measured as described above.

Statistical Analyses.

Tumor volume measurements for in vivo models were analyzed under a cubic root transformation to stabilize the variance as in Morse et al. 2010. Welch t-tests were used to assess differences between mice injected with HER3-VIA or control GFP-VIA. Analyses were performed using R version 2.10.1. For all tests, statistical significance was set at $p<0.05$.

Results

Ad-HER3 Elicits Anti-HER3 T Cell and Antibody Responses In Vivo

Figure 1C:
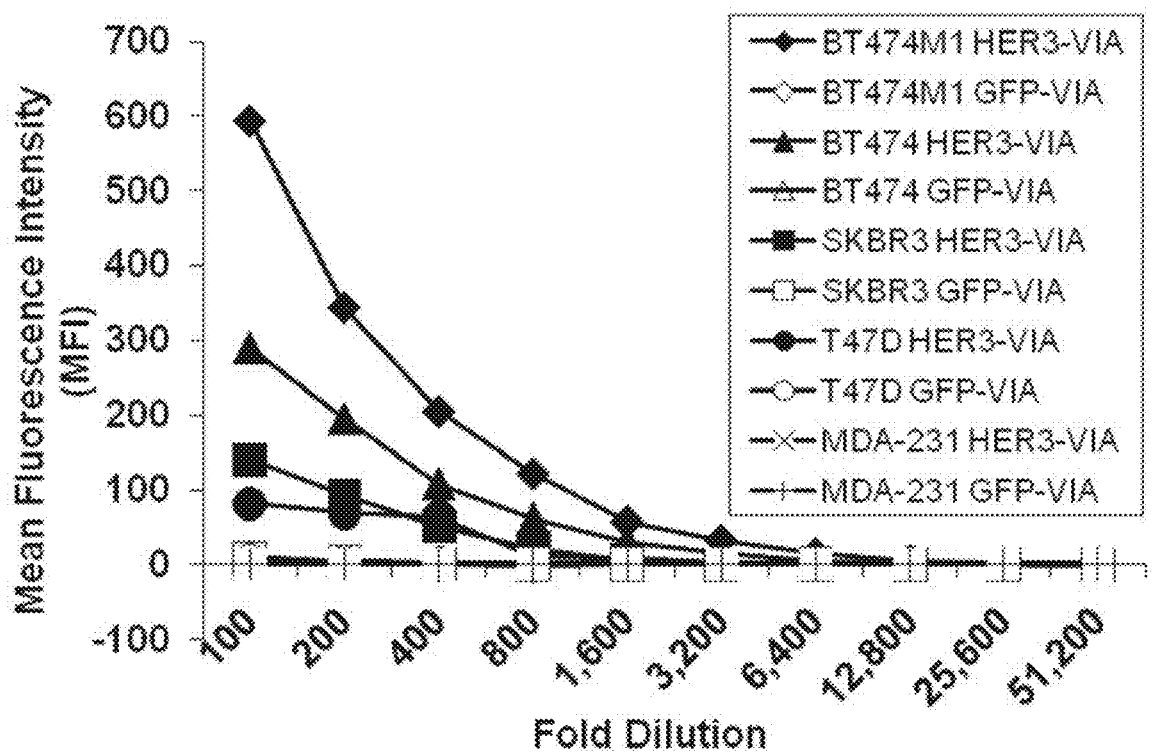
Figure 1B:
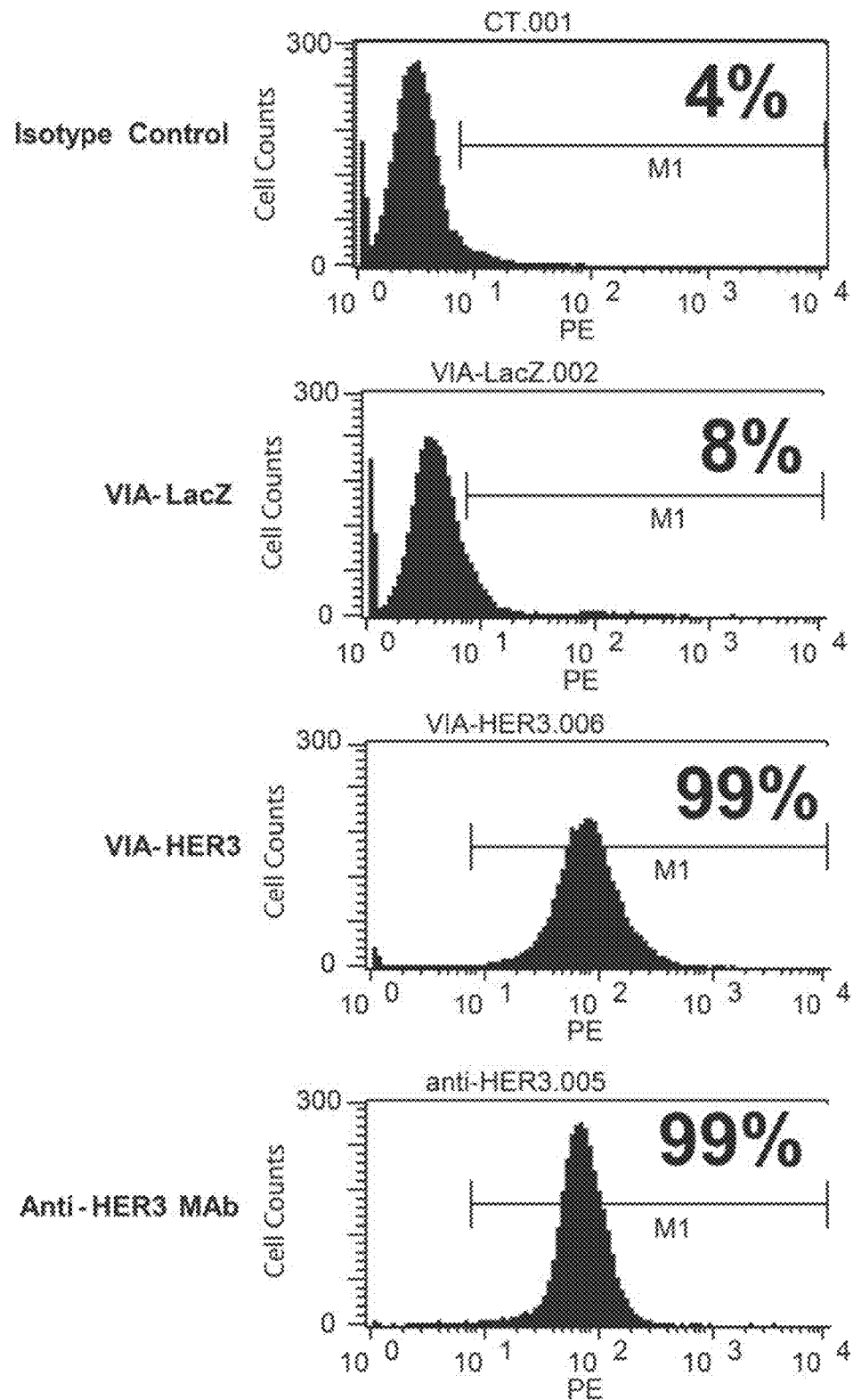

We developed a recombinant E1−, E3− adenovirus serotype 5 vector (Ad-HER3) expressing full length human HER3 (Ad-HER3). Wild type BALB/c mice were vaccinated with Ad-HER3, splenocytes from vaccinated mice were harvested and demonstrated by ELISPOT to specifically recognize HER3 using an overlapping human HER3 peptide mix as a source of antigens, whereas splenocytes from mice receiving control Ad-GFP vaccine or saline showed no reactivity to the HER3 peptide mix (FIG. 1A). To detect HER3-specific antibodies capable of detecting membrane associated HER3, binding of vaccine induced antibodies (VIA) in mouse serum was tested using a series of human HER3 expressing breast tumor cells lines, including the high HERS expressing BT474M1, BT474, SKBR3 and T47D and the low to negatively expressing MDA-231 tumor cell line (FIGS. 1B and 1C). The serum of mice vaccinated with the Ad-HER3 had binding titers of >1:800, whereas the serum of mice receiving the control Ad-LacZ vaccine showed only background levels of binding. Thus, HER3-VIA are able to bind to endogenous HER3 expressed on human breast cancer lines.

To confirm that multiple HERS epitopes were recognized, we demonstrated VIA binding to a series of HERS peptides. The HERS-VIA recognized at least 18 epitopes in both the intracellular and extracellular domain, demonstrating that the antibody responses are polyclonal (FIG. 1D and SEQ ID NOs: 5-22), It should be noted that peptide arrays do not recapitulate conformationally correct protein structure, so they often underestimate the true number of epitopes recognized.

Figure 2A:
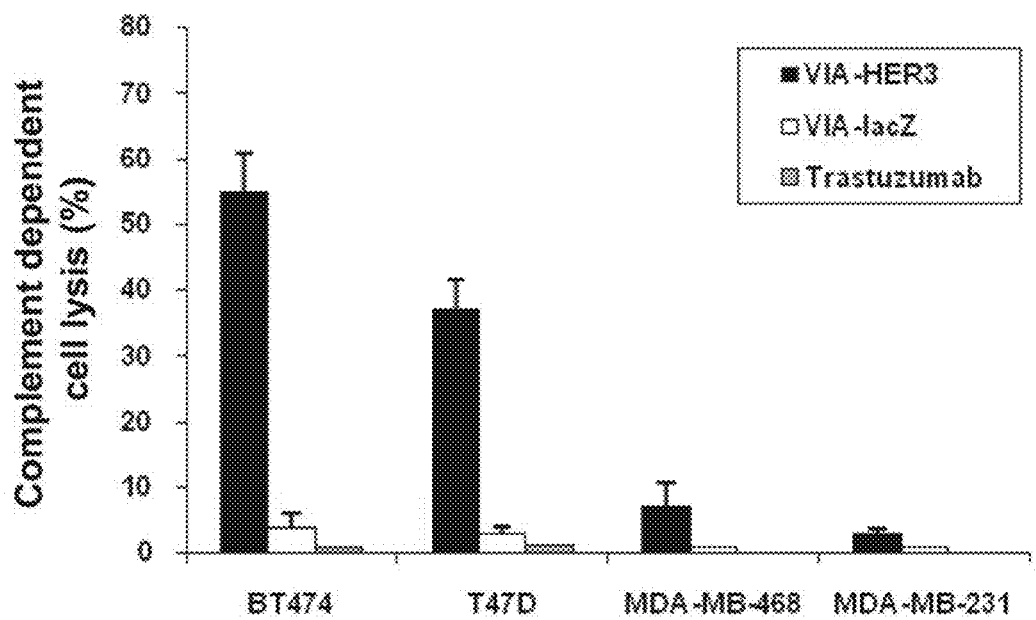
FIG. 2A-2C is a set of figures showing that HER3-VIA mediate multiple mechanisms of action on human breast tumor cell lines in vitro.
Figure 2A:
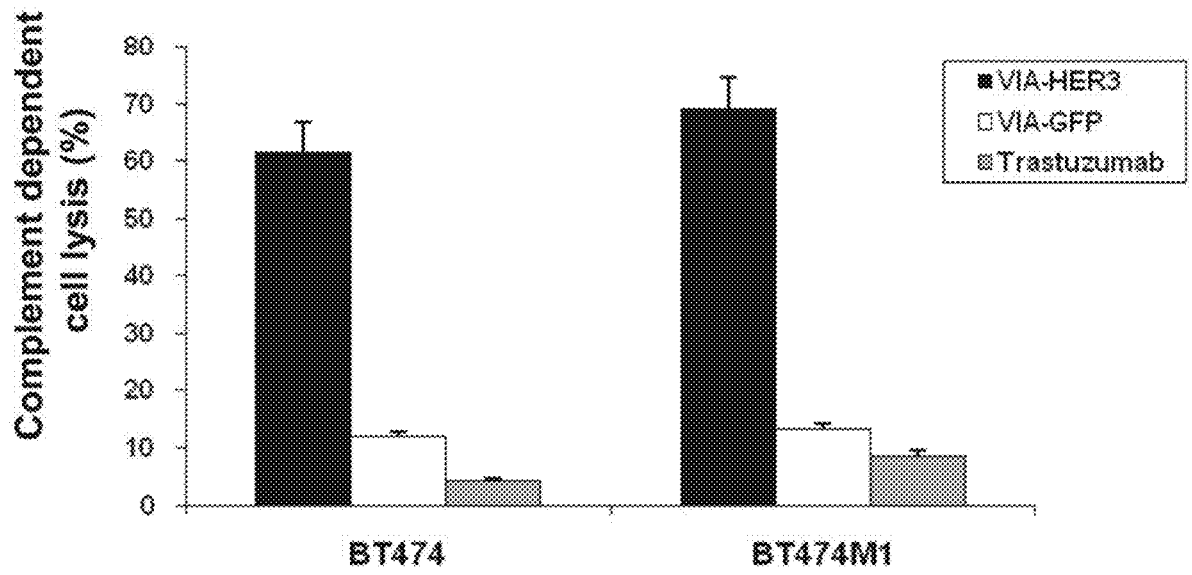

HER3 Specific Antibodies Induced by Vaccination (HER3-VIA) Mediate Complement Dependent Lysis of HER3+ Breast Tumor Cell Lines In Vitro Direct antibody-mediated tumor cell killing is a powerful potential mechanism of action of antibodies induced by vaccination. We evaluated the capacity HERS-VIA to mediate complement-dependent cytotoxicity (CDC). HERS-VIA exhibited strong CDC against HERS-expressing human breast tumor cells but not the HERS negative MDA-231 cell line, while control CEP-VIA showed no effect (FIG. 2A). Trastuzumab is known not to mediate CDC and this was confirmed in our assays.

Anti-Proliferative Effects of HER3 VIA In Vitro

Figure 2B:
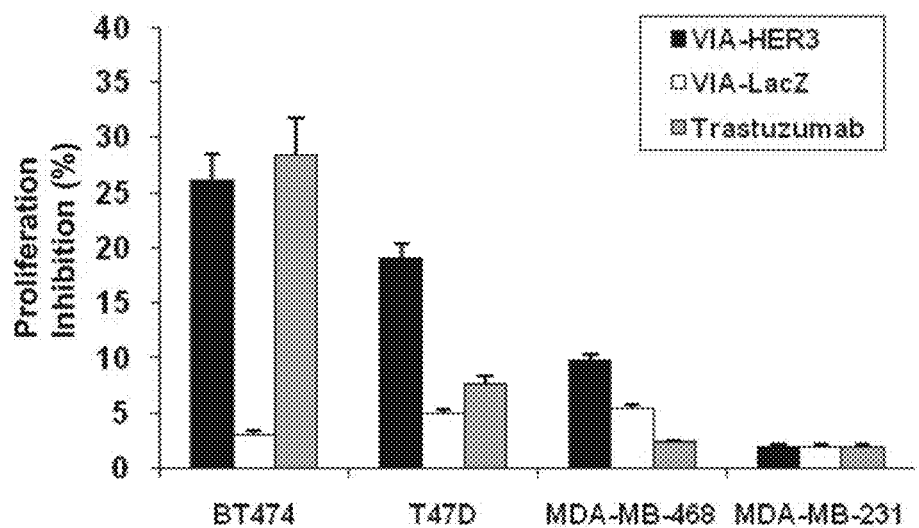
Figure 2B:
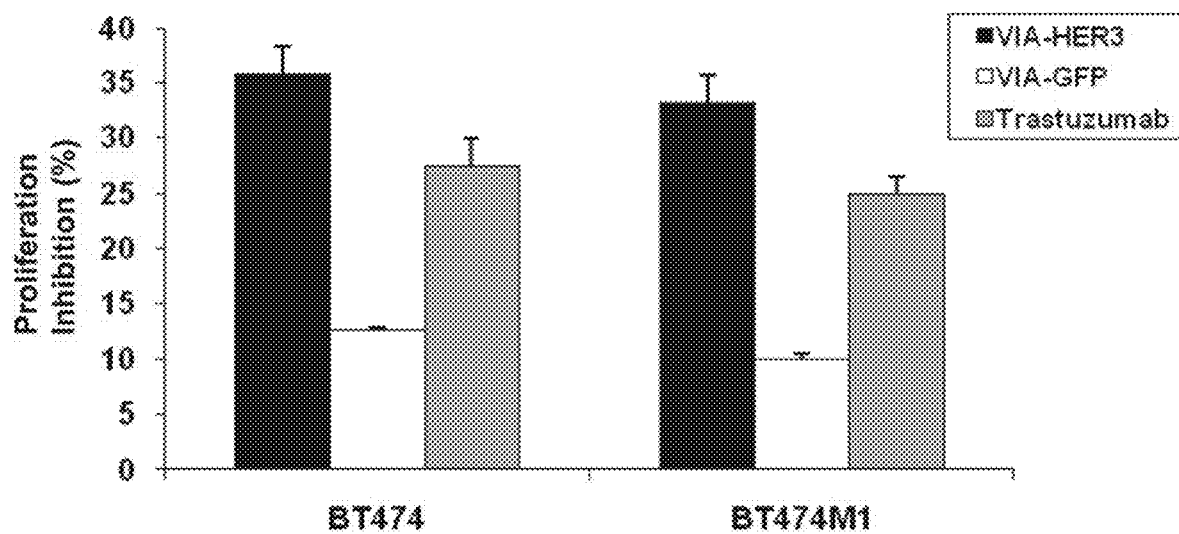

Although immunization with Ad-HERS was able to efficiently induce humoral immunity in vivo and mediate complement dependent tumor cell cytotoxicity, we also wished to determine whether these antibodies could inhibit tumor cell proliferation, We found that when HERS-expressing human breast cancer cells were cultured with HERS-VIA from the sera of Ad-HERS vaccinated mice, their proliferation was significantly, inhibited compared with cells cultured with control CFP-VIA (FIG. 2B). Of interest, despite the much high levels of HER2 expressed on these tumor cells, compared to HERS, the inhibition of tumor cell proliferation mediated by HER3-VIA was similar to the effects of the clinically effective monoclonal antibody trastuzumab.

Loss of HER3 Expression on Tumor Cell Lines Mediated by HER3-VIA In Vitro

Figure 2C:
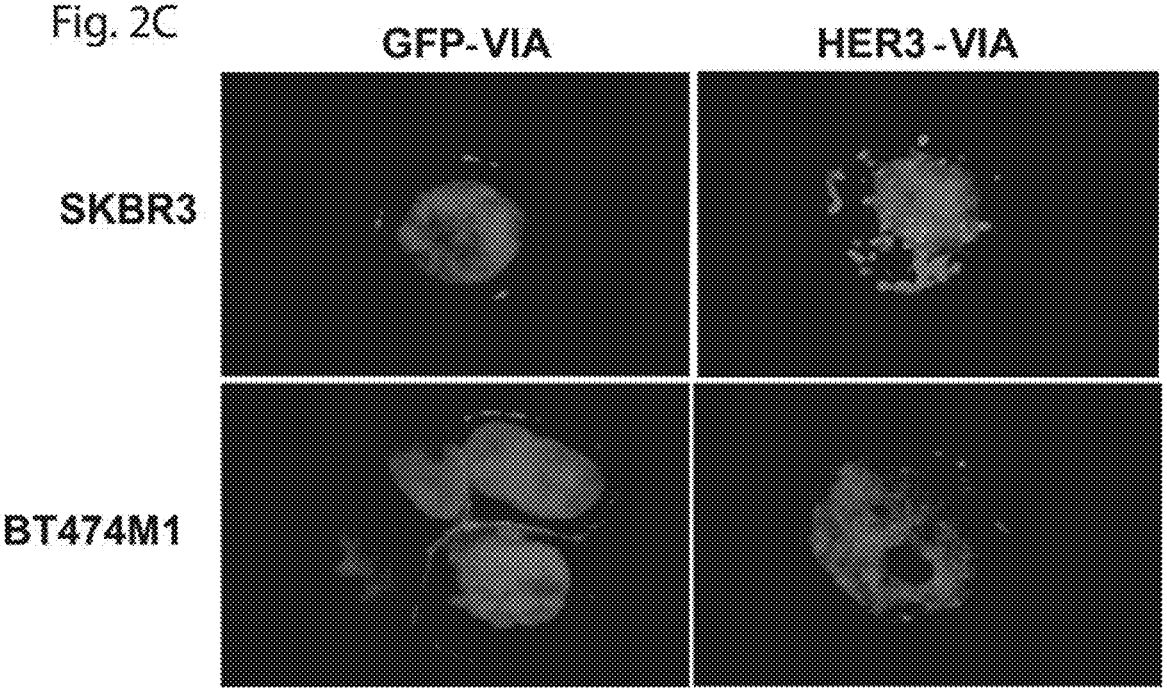

Growth factor receptor internalization, degradation, and down regulation has been proposed as a mechanism for the inhibition of tumor growth mediated by monoclonal antibodies. To ascertain whether receptor down regulation was caused by HER3-VIA as a result of receptor internalization, we visualized cell membrane associated HER3 receptor on SKBR3 and BT474M1 tumor cells. When exposed to serum containing HER3-VIA or GFP-VIA, dramatic internalization and aggregation of the receptor was observed within 1 hr after exposure to HER3-VIA, but not with exposure to control GFP-VIA (FIG. 2C).

Figure 3A:
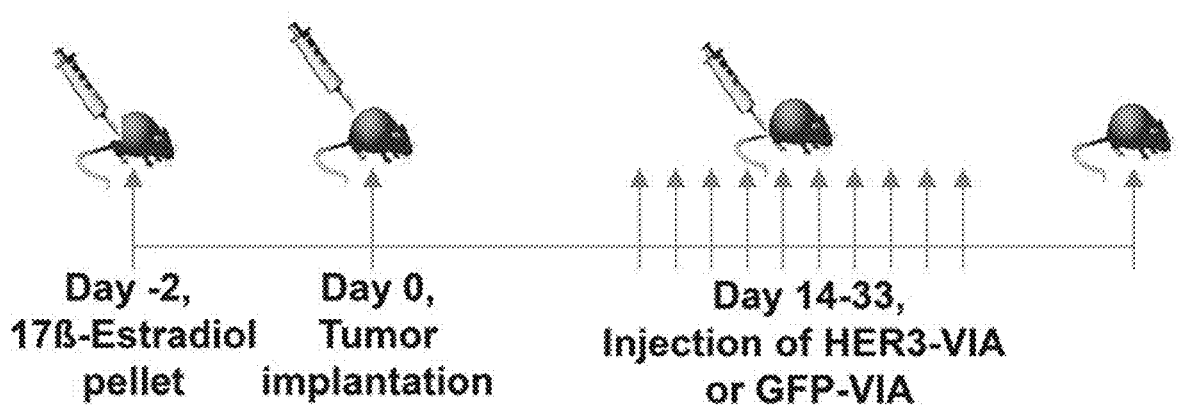
Figure 3B:
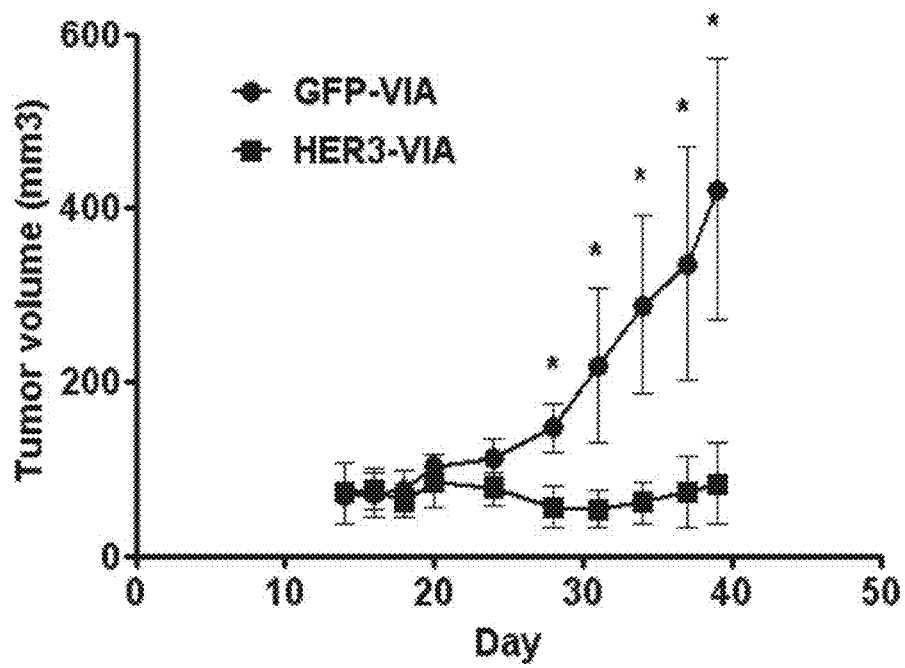

Inhibition of Tumor Growth by HER3 VIA In Vivo is Associated with Loss of HER3 Expression and Anti-Signaling Effects After finding that HER3 specific antibodies could inhibit HER3+ tumor cell proliferation in vitro, we sought to demonstrate the effects of HER3 VIA in vivo. At this time, there are no murine breast tumors dependent on human HER3 for growth, and attempts to establish 4T1 tumors expressing HER3 have been unsuccessful. Consequently, we employed a human xenograft model using the BT474M1 cell line that expresses both HER2 and HER3, with adoptive transfer of antibodies to demonstrate the in vivo activity of HER3-VIA. The study design is illustrated in FIG. 3A. We found that passive immunotherapy with HER3-VIA retarded the growth of established HER3+BT474M1 human tumor xenografts in vivo (p<0.005 after Day 28) when compared to the control GFP-VIA treated mice (FIG. 3B). At the termination of the study tumor size was compared and was significantly reduced in the HER3-VIA-treated mice (p=0.005).

Figure 3C:
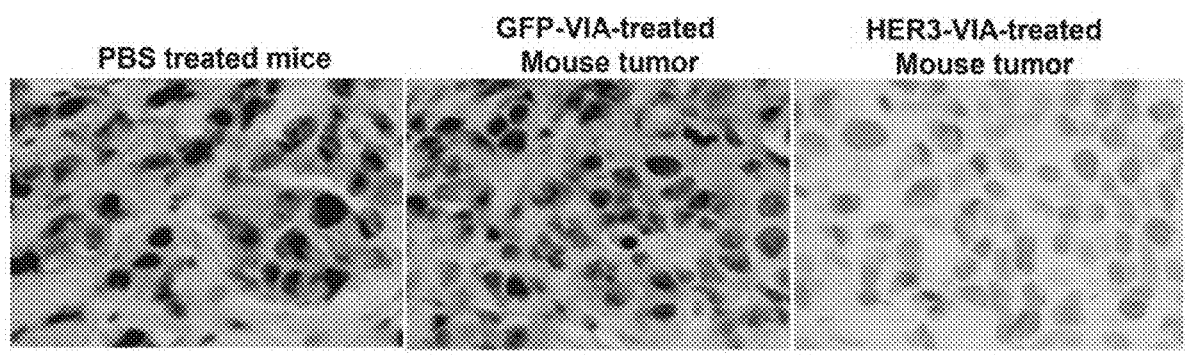

In addition to demonstrating anti-tumor effects in vivo, we also wanted to document the anti-HER3 signaling effects of HER3 VIA in vivo. Analysis of excised tumors allowed us to determine HER3 expression following treatment in vivo. We found that mice treated with HER3-VIA showed decreased levels of HER3 in their residual tumor by immunohistochemistry (FIG. 3C), consistent with antigen down-regulation as the basis of immunologic escape. We also examined the impact of treatment with HER3-VIA on downstream effectors of HER3 signaling, and found a reduction of pHER (pTyr), HER3, and pErk1/2, compared to tumors treated with GFP-VIA (FIG. 3D).

Inhibition of Therapy-Resistant Tumor Growth by HER3 VIA In Vivo

Figure 4A:
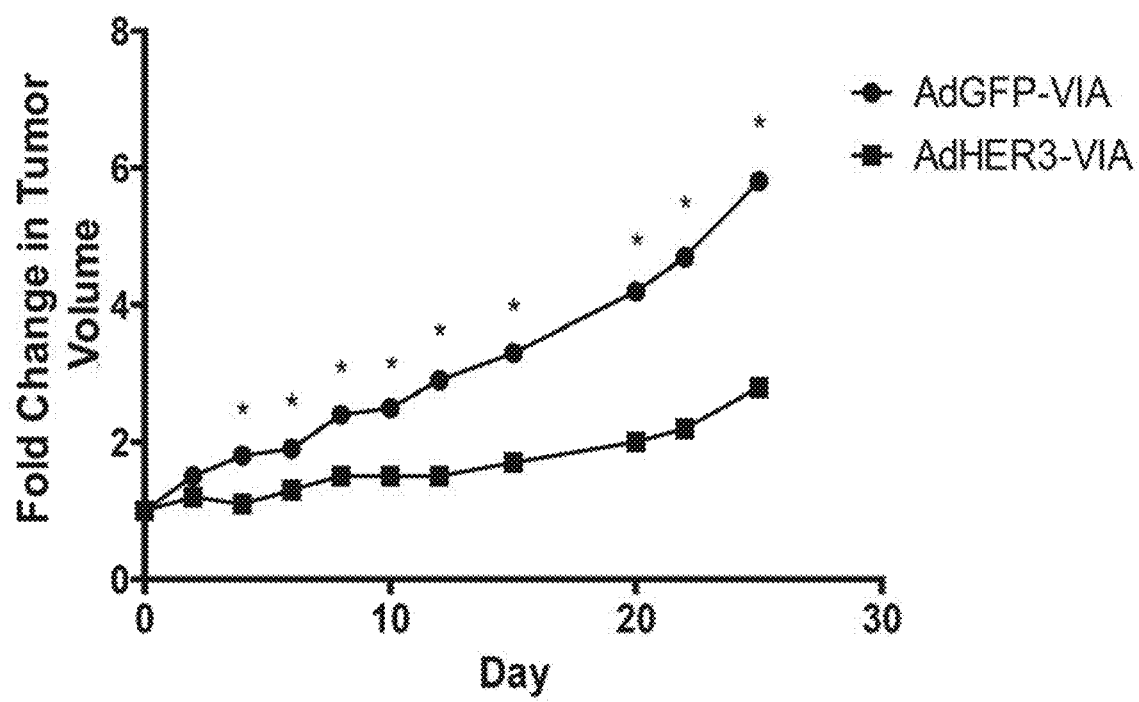
FIG. 4A-4C is a set of figures showing the in vivo effects of HER3-VIA in lapatinib-refractory rBT474 SCID tumor xenografts.

While the antitumor efficacy against established HER3+ BT474M1 tumors was encouraging, we know that a major unmet need for breast cancer patients is for therapies to overcome therapeutic resistance to HER2 targeted therapies. For example, therapeutic resistance to trastuzumab, can be overcome by treatment with a small molecule inhibitor of HER2, lapatinib, but patients whose tumors initially respond ultimately experience therapeutic resistance and disease progression. Of interest is the persistent overexpression of HER2 in the tumors from these patients, and the emerging recognition that signaling from the HER2/HER3 heterodimer, and other heterodimers involving HER3, was a significant resistance mechanism. Consequently, we tested the effects of HER3-VIA in a model of lapatinib resistance derived from the rBT474 cell line that we have previously reported. Xia et al. A model of acquired autoresistance to a potent ErbB2 tyrosine kinase inhibitor and a therapeutic strategy to prevent its onset in breast cancer. Proc Natl Acad Sci USA 2006; 103:7795-800. This rBT474 cell line expresses HER2 and HER3 at similar levels to the BT474M1 tumor line. We demonstrate that the HER3-VIA was effective at retarding the growth of established tumors (FIG. 4A) (p 0.025 for all time points from Day 4 to Day 25), confirming the therapeutic potential of an Ad-HER3 vaccine for patients who have experienced disease progression on lapatinib.

Figure 4C:
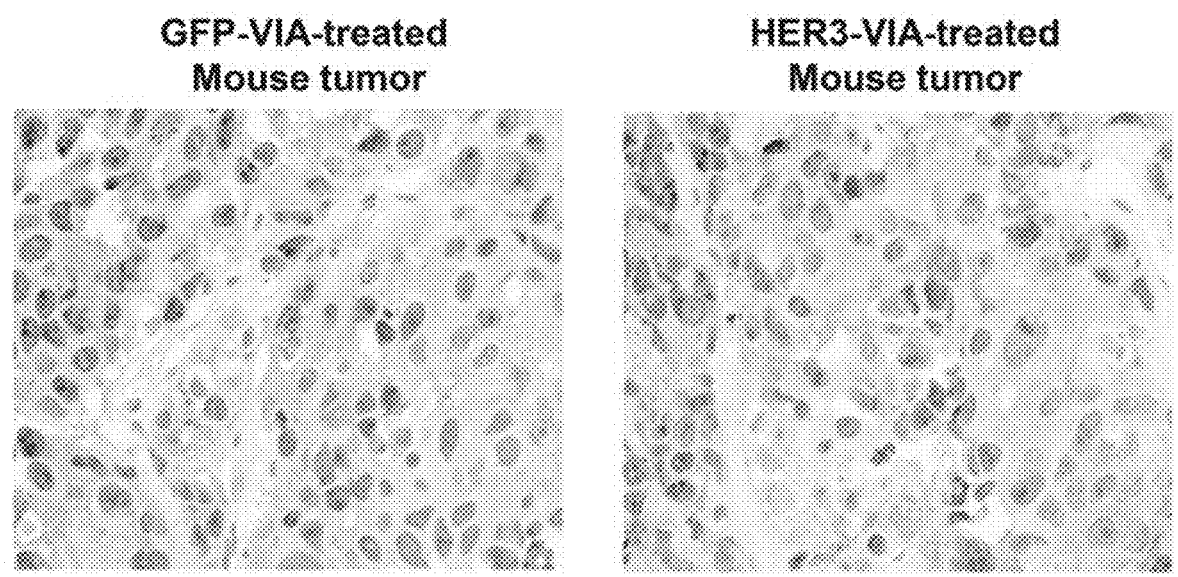
Figure 4B:
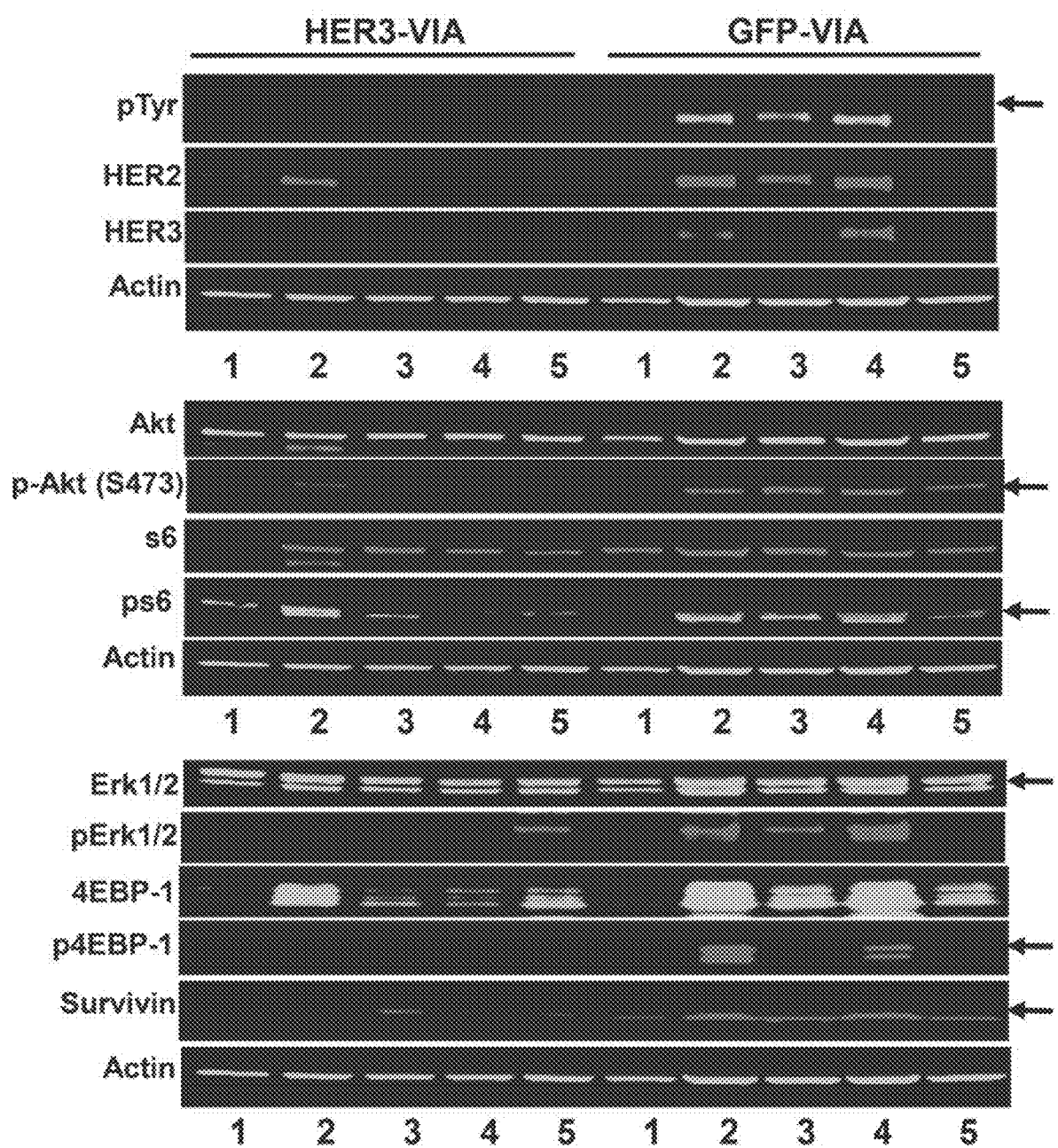

Inhibition of Lapatinib-Resistant Tumor Growth by HER3 VIA In Vivo is Associated with Loss of HER3 Expression and Broader Anti-Signaling Effects than Lapatinib-Sensitive Tumors Tumors excised from the mice at the termination of the study described above, were examined for signaling pathway modulation. Whole tumor lysates from 5 mice per group were studied, since we expected some mouse-to-mouse variation and wanted to capture the spectrum of responses (FIG. 4B). Total HER2 and HER3 levels are decreased in the HER3-VIA treated tumors, suggesting receptor degradation may be occurring. pTyr is also consequently reduced, indicating decreased HER2:HER3 signaling. pAkt473(S473) and pS6 are also decreased for the HER3-VIA treated tumors, as are pErk1/2, p4EBP1, and survivin relative to the control GFP-VIA treated tumors. In contrast to the data in the lapatinib-sensitive BT474M1 tumors, immunohistochemistry analysis of excised rBT474 tumors did not show a marked decrease in HER3 in tumors treated with HER3-VIA compared to GFP-VIA controls (FIG. 4C), suggesting that HER3 degradation was more modest and anti-proliferative effects mediated through the HER3 heterodimers were therefore more prominent.

Generate Ad5(E2b-)HER3 and Ad5(E2b-)HER3 C1C2 Constructs (Y1, Q1-2)

Adenoviral vectors expressing HER3 using the Ad5 (E2b-) platform have been constructed and have been used to generate virus. We now wanted to assess whether other HER3 expressing adenovirus vectors would have similar effects. We have modified the adenovirus construction methods to facilitate the construction of (E1-, E2b-, E3-) Ad5 vector.

Figure 5:
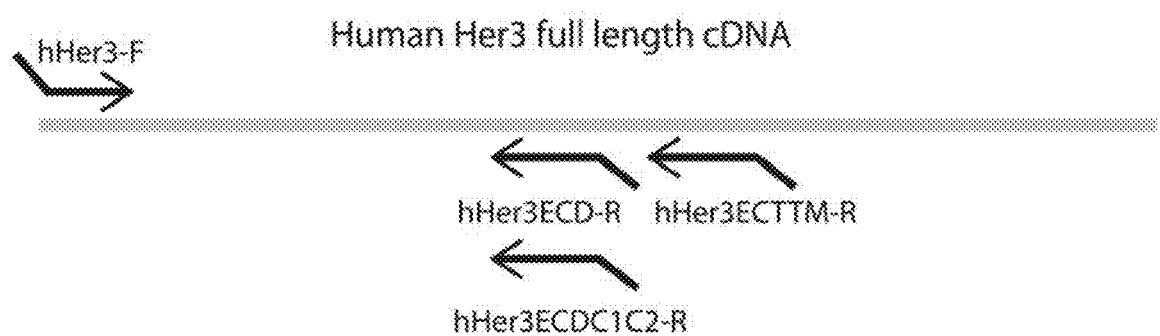
FIG. 5 is a schematic representation of the primer binding sites on the human Her3 full length cDNA.

The human HER3 full length cDNA was obtained from OriGene (Rockville, Md.). The truncated HER3 extracellular domain (ECD) and HER3 ECD plus transmembrane (TM) sequence were created using HER3 full length as templates in a PCR reaction using primers (see Table 1 below) and FIG. 5.

TABLE 1

Primers used in construction of truncated Ad5-human HER3

| Primer | Sequence (SEQ ID NO:) |
|---|---|
| hHER3-F | 5'-cagggcggccgcaccatgagggcgaacgacgctct-3' (SEQ ID NO: 23) |
| hHER3-ECDTM-R | 5'-acaagcggccgcagttaaaaagtgccgcccagcatca-3' (SEQ ID NO: 24) |
| hHER3-ECD-R | 5'-acaagcggccgcatttatgtcagatgggttttgccgatc-3' (SEQ ID NO: 25) |
| hHER3-ECDC1C2-R | 5'-acaagcggccgcattgtcagatgggttttgccg-3' (SEQ ID NO: 26) |

Briefly, full length HER3 cDNA and the PCR product are cut by restrict enzyme Not I and subcloned into Not I digested pShuttle-CMV or pShuttleCMV-C1C2 plasmid. Confirmation of correct insert of the full length and truncated DNA within pShuttle-CMV or pShuttle-CMV-C1C2 was confirmed by DNA sequencing. The pShuttle-CMV-her3-FL (full-length), pShuttle-Her3ECD, pShuttle-Her3ECD™ and pShuttle-Her3ECDC1C2 were then linearized using digestion with Pme I, recombined into linearized (E1-, E2b-, E3-) serotype 5 pAd construct in BJ 5183 bacterial recombination-based system (Stratagene), and propagated in XL10-Gold Ultracompetent cells (Stratagene). Complementing C7 cell (which express E1 and E2b) were used to produce high titers of these replication-deficient Ad5 vectors, and cesium chloride density gradient was done to purify the Ad5-vectors. All Ad vectors stocks were evaluated for replication-competent adenovirus via PCR-based replication-competent adenovirus assay.

The next generation human HER3 (E1−, E2b−, E3−) Adenovirus vectors are as follows:
1. Ad5 (E2b−)HER3 FL; express human HER3 full length.
2. Ad5 (E2b−)HER3ECD™; express human HER3 ECD and trans-membrane domain
3. Ad5 (E2b−)HER3ECD; express human HER3 ECD
4. Ad5 (E2b−)HER3ECDC1C2; express human HER3 ECD and C1C2 domain The ability of each vector to induce a HER3 specific immune responses will be tested, but was expected based on the earlier results and epitopes identified above. Human HER3 specific immune responses to the vectors will be measured in Balb/c mice and in human HER3 transgenic mice.

Figure 6:
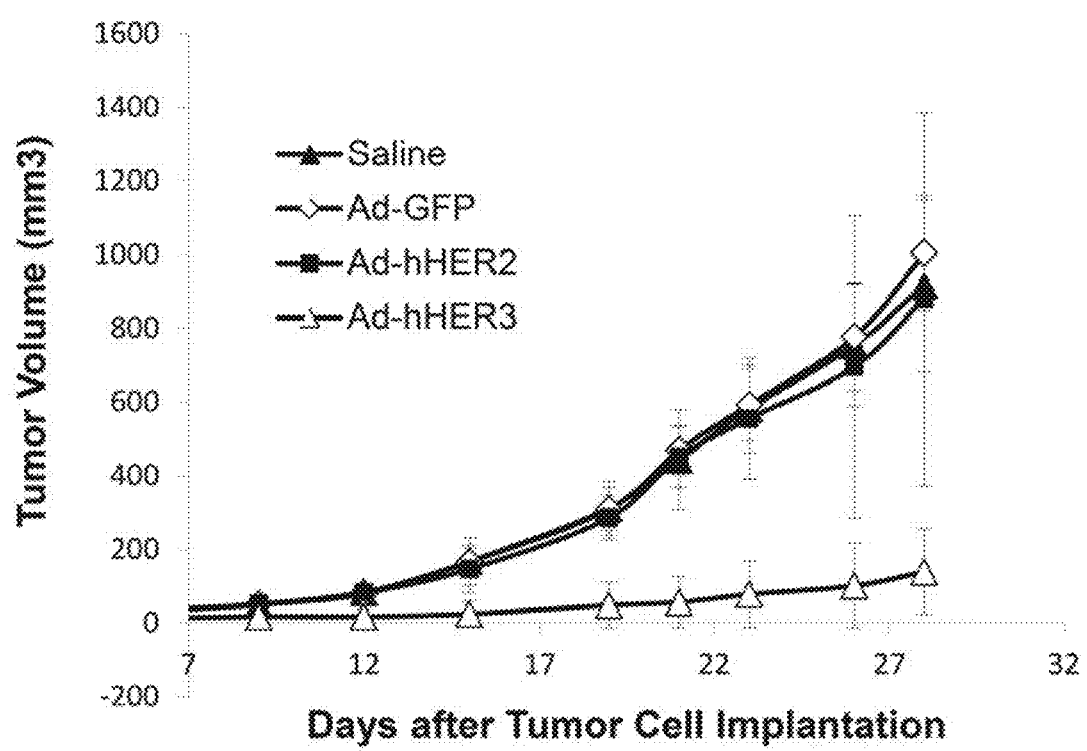
FIG. 6 is a graph showing that Ad-HER3 vaccine inhibits JC-HER3 tumor growth. Balb/c mice were vaccinated twice (day-18, day-4) via footpad injection with Ad-GFP or Ad-hHER3 vectors ($2.6 \times 10^{10}$ particles/mouse). Four days after boosting, at day 0, each mouse was implanted with 1,000,000 JC-HER3 mouse mammary tumor cells expressing human HER3. Tumor volume was measured, once it became palpable, every 3 days using calipers and is reported.
Figure 7:
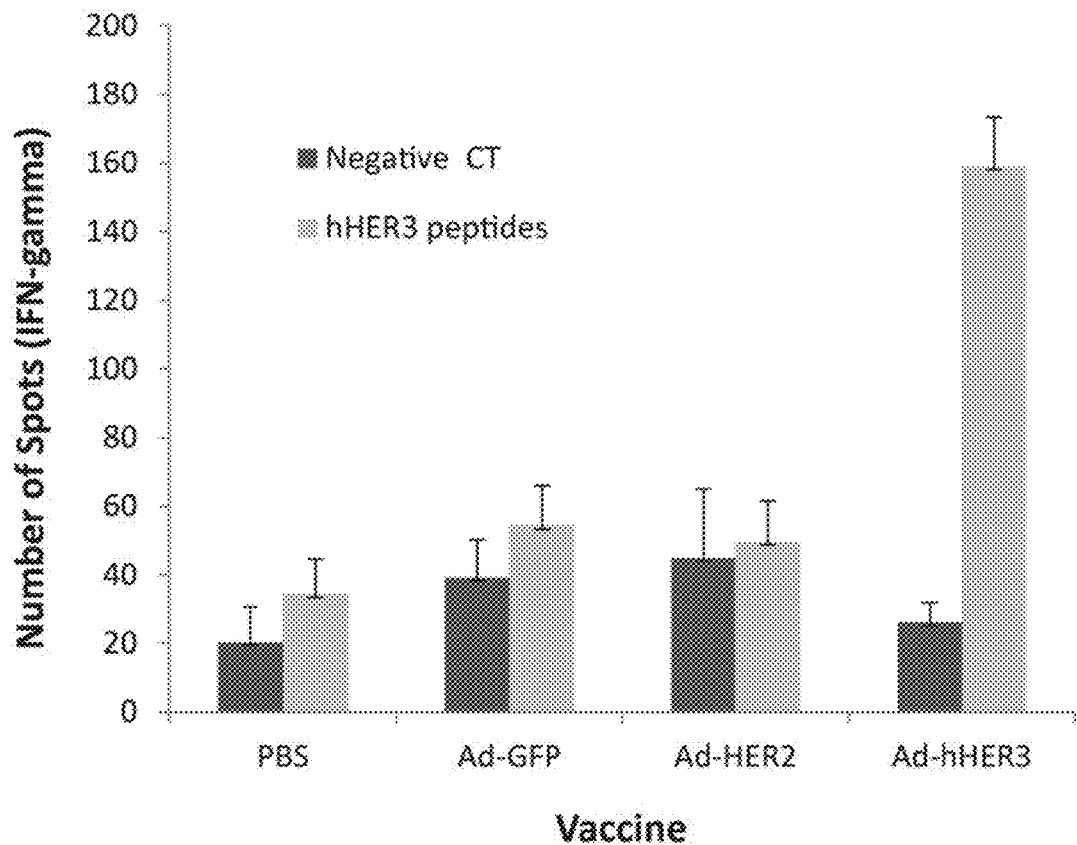
FIG. 7 is a graph showing Ad-hHER3 vaccine induced HER3 specific T cell response. Splenocytes (500,000 cells/well) from vaccinated Balb/c mice in FIG. 6 (x-axis) were collected at day 28 and stimulated with HER3 peptide mix (hHER3 peptides) (1 μg/mL was used; JPT, Acton, Mass.) or HIV peptide mix (BD Bioscience) as a negative control (Negative CT) and analyzed in a interferon-gamma ELISpot assay.

To determine the preventive effect of HER3 vaccination, we have established a HER3 prevention model using JC-HER3 mouse mammary tumor cells in Balb/c mice. As shown in FIG. 6, only vaccination with the HER3 encoding vector prevented growth of the hHER3 expressing tumors in vivo. We next sought to demonstrate development of HER3 specific immune response by ELISPOT. Results are shown in FIG. 7.

Figure 8:
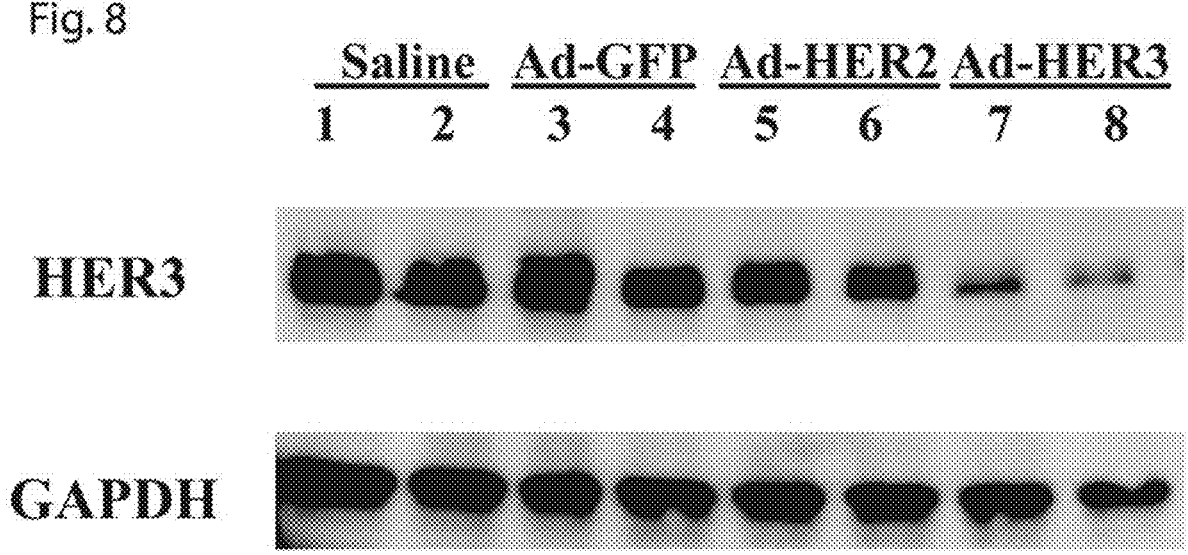
FIG. 8 is a set of photographs showing that Ad-hHER3 vaccination causes degradation of HER3 on JC-hHER3 tumor. Tumors were isolated from vaccinated and control Balb/c mice (as indicated on figure) and immediately flash frozen. Tissue extracts were prepared by homogenization in RIPA buffer. Equal amounts of protein from each sample were used to visualize the indicated molecules by immunoblotting.

Due to the induction of HER3 specific immune responses, we sought evidence whether those tumors that did grow in the HER3 vaccinated mice expressed HER3. In other words, we sought evidence of loss of HER3 in those tumors capable of growth in the vaccinated mice. As shown in FIG. 8, immunization with Ad-hHER3 led to a reduction of HER3 expression in the tumors that did develop. Of interest, immunization with Ad-GFP or Ad-hHER2 did not change HER3 expression.

Figure 9:
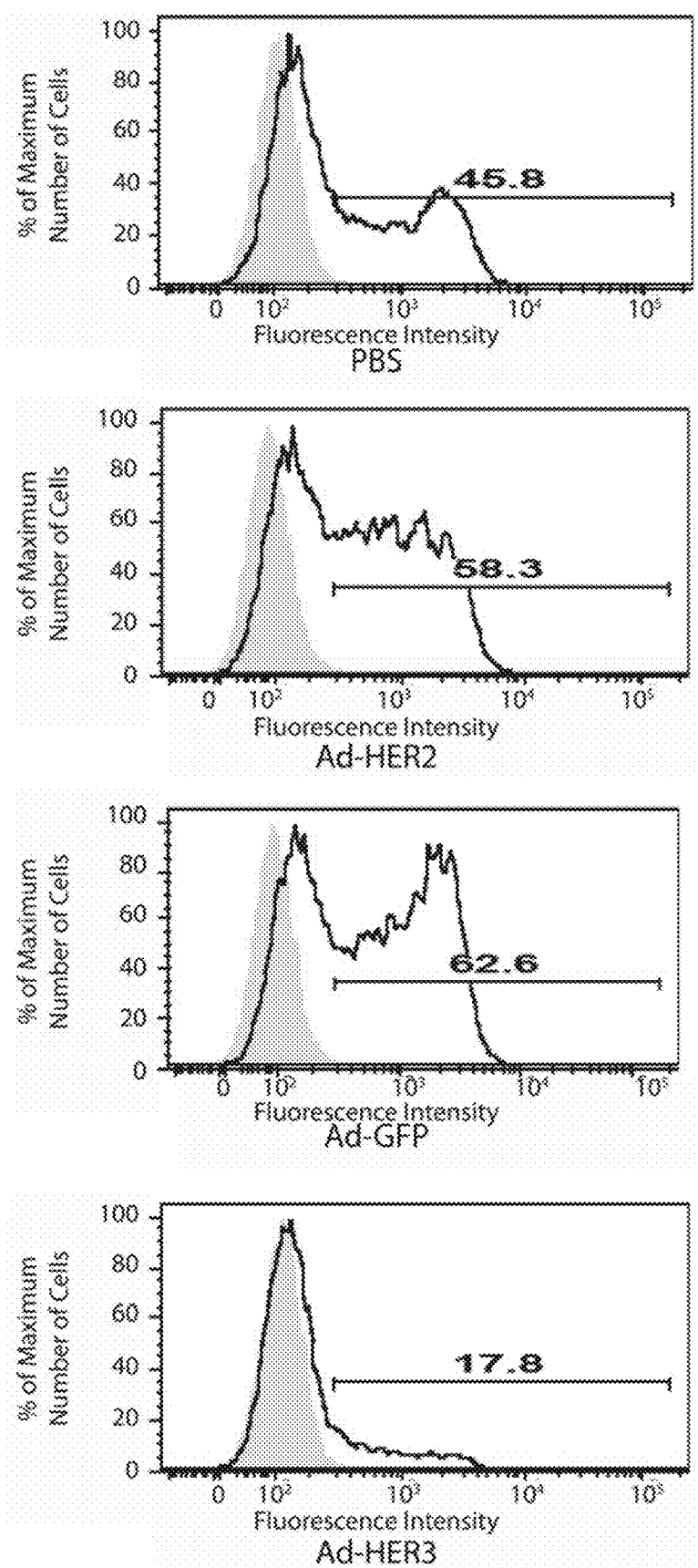
FIG. 9 is a set of FACS histograms showing that Ad-hHER3 vaccination decreases HER3 expression on JC-hHER3 tumor cells. JC-HER3 tumors were collected from vaccinated and control Balb/c mice (as indicated on figure) at day 28 and pooled by group. The tissues were minced and digested with an enzymatic cocktail (Hyaluronalse, DNAse, and Collagenase) overnight. After 3 days culture, the cells were harvested and HER3 expression determined by flow cytometry using PE-anti-hHER3 antibody.

We then tested for surface HER3 expression in the tumors that grew in the HER3 vaccinated mice. As demonstrated in FIG. 9, the surface expression of HER3 was dramatically reduced in the tumors that did grow in the HER3 vaccinated mice.

In summary, we created a HER3 vaccine by generating a recombinant adenovirus encoding human HER3 (Ad-HER3). The Ad-HER3 was highly effective in eliciting significant HER3 specific T-cell and polyclonal antibody responses in mouse models, with the vaccine induced antibodies (VIA) binding multiple HER3 epitopes as well as tumor-expressed HER3 and mediating complement dependent lysis. In addition, the HER3-VIA caused HER3 internalization and degradation, significantly inhibited signaling mediated by receptor heterdimers involving HER3, and retarded tumor growth in vitro and in vivo. Critically, we also showed that the HER3-VIA retarded the growth of human breast cancer refractory to HER2 small molecule inhibitors (lapatinib) in SCID xenografts, providing a compelling argument for the Ad-HER3 vaccine to be tested in patients whose cancer has progressed on HER2 targeted therapy, and in combination with HER2 targeted therapy.

It is interesting to note that the lapatinib-resistant rBT474 clone is much more sensitive to HER3-VIA in vivo than the lapatinib-sensitive BT474M1 clone yet they express equivalent levels of HER3 on the cell surface, which may be a result of increased reliance on HER3 as a driver of tumor growth in the lapatinib resistant BT474 cells. In fact, treatment of the lapatinib resistant BT474 cells leads to decreased HER3, pHER3 and pERK1/2 as expected, but also decreased HER2, pAkt(5473), pS6, p4EPB1, and survivin expression. In contrast, treatment of the lapatinib sensitive BT474 cells with HER3 VIA decreases only HER3, pHER3 and pErk1/2, suggesting that HER3 VIA will have more profound biologic and clinical effects in lapatinib refractory tumors. The lapatinib-resistant BT474 cells also continue to express HER3 protein after treatment with HER3-VIA in vivo, suggesting that antigen loss is not an escape mechanism for lapatinib resistant tumors because HER3 is critical to the tumor survival. Thus, persistent expression of HER3 because of it' role in lapatinib resistance, ensures that tumors will remain targets for vaccine induced T cell and antibody response.

The decrease in the inhibitor of apoptosis protein survivin suggests that a mechanism of resistance to tumor cell killing is also being diminished. We observed similar effects on the expression of survivin in the mouse 4T1-HER2 tumor model which is relatively resistant to trastuzumab, but relatively sensitive to lapatinib. When the 4T1-HER2 expressing tumors were treated with lapatinib or HER2 VIA alone, we observed no change in survivin expression, but when these tumors were treated with a combination of lapatinib and HER2-VIA we observed a decrease in survivin expression, implying that complete HER2 signaling blockade decreased survivin expression. In an analogous fashion, it suggested that complete blockade of HER2:HER3 signaling in lapatinib refractory tumors is accomplished by treatment with HER3-VIA, resulting in the decreased expression of survivin in these studies.

We believe our findings have relevance for counteracting the development of resistance to HER2 targeted therapies. Although HER3 is non-transforming alone, recent data suggests that HER3 expression or signaling is associated with drug resistance to targeted therapies directed against other HER family members. In particular, the acquired resistance to HER2 inhibitors in HER2-amplified breast cancers, trastuzumab resistance in breast cancer, with EGFR inhibitors in lung cancers, with pertuzumab resistance in ovarian cancers, and with EGFR inhibitors in head and neck cancers. The overexpression of HER2:HER3 heterodimers is also negatively correlated with survival in breast cancer. Our approach of targeting HER3 may also have advantages over other HER family targeting strategies. For example, data suggest that trastuzumab is effective against HER1:HER2 heterodimers but not HER2:HER3 heterodimers. HER3 may play a role in therapeutic resistance to other therapies including anti-estrogen therapies in ER positive breast cancers, with hormone resistance in prostate cancers, and with IGF1R inhibitors in hepatomas. Therefore, targeting HER3 may have relevance for counteracting resistance to other pathway inhibitors.

These data suggest that it may be possible to begin a "resistance prophylaxis" vaccination against overexpressed or mutated proteins that will predictably arise to mediate therapeutic resistance, such as HER3. Immunization against these proteins prior to their overexpression as a mediator of therapeutic resistance may avoid immune tolerance induced by their prolonged expression in an immunosuppressive microenvironment. The resulting pre-existing immune response would be much more effective in mediating anti-tumor responses to tumors overexpressing antigen, and/or prevent these mediators from being expressed.

We claim:

1. A vaccine comprising a vector operably connected to a polynucleotide encoding a HER3 polypeptide, wherein the HER3 polypeptide consists of at least one of SEQ ID NOs: 5-8 and 10-22.

2. The vaccine of claim 1, wherein the vaccine vector expresses the HER3 polypeptide.

3. The vaccine of claim 1, wherein the vaccine vector is selected from adenovirus or adeno-associated virus (AAV).

4. A method of treating a cancer or precancer or of reducing the likelihood of the cancer developing resistance to a cancer therapeutic comprising administering the vaccine of claim 1 to a subject having the cancer or precancer, wherein administration of the vaccine to the subject treats the cancer or precancer, reduces the likelihood of the cancer or precancer developing resistance to the cancer therapeutic or reverses resistance of the cancer or precancer to the cancer therapeutic.

5. The method of claim 4, wherein the vaccine is administered concurrently with, before or after administration of the cancer therapeutic.

6. The method of claim 5, wherein the cancer therapeutic is an agent targeting HER2, HER1, estrogen receptor, EGFR, or IGF1R or is selected from the group consisting of trastuzumab, lapatinib, cetuximab, pertuzumab and erlotinib.

7. The method of claim 4, wherein the cancer or precancer is selected from the group consisting of a breast, prostate, lung, ovarian, colon, rectal, pancreas, bladder, head and neck, liver and HER2 positive cancer or precancer.

8. The method of claim 4, wherein the subject develops an immune response to HER3.

9. The method of claim 8, wherein the immune response includes at least one of antibody-dependent cellular cytotoxicity, polyclonal antibody response, complement dependent cellular cytotoxicity, cellular cytotoxicity, disruption of ligand binding, disruption of dimerization, mimicking ligand binding causing internalization of HER3, an antibody response, a T cell mediated response or degradation of HER3.

10. The method of claim 8, wherein the immune response comprises an antibody response directed to at least one of SEQ ID NOs: 5-8 and 10-22.

11. The method of claim 4, wherein administration of the vaccine results in a reduction of HER3 expression on cancer or precancer cells after administration of the vaccine as compared to the level of HER3 on the cells prior to vaccination.

12. The method of claim 4, wherein administration results in decreased tumor growth rate or decreased tumor size after administration as compared to prior to administration.

13. A method of reducing the likelihood of a cancer or precancer developing resistance to a cancer therapeutic comprising administering the cancer therapeutic and a vaccine of claim 1, wherein the expression or activation of HER3 is correlated with development of resistance of the cancer or precancer to the cancer therapeutic to a subject having a cancer or precancer.

14. The method of claim 13, wherein administration reduces the growth of the cancer or precancer.

15. The method of claim 13, wherein the cancer does not develop resistance to the cancer therapeutic or wherein cancer or precancer that is resistant to the cancer therapeutic becomes more sensitive to the cancer therapeutic after administration of the vaccine.

16. The method of claim 13, wherein the vaccine is administered concurrently with, before or after administration of the cancer therapeutic.

17. The vaccine of claim 1, wherein the vaccine vector comprises is a human cytomegalovirus (CMV) promoter.

* * * * *

SEQUENCE LISTING

<160> NUMBER OF SEQ ID NOS: 26

<210> SEQ ID NO 1
<211> LENGTH: 331
<212> TYPE: PRT
<213> ORGANISM: Homo sapiens
<220> FEATURE:
<221> NAME/KEY: misc_feature
<223> OTHER INFORMATION: Human HER3 Protein amino acid sequence

<400> SEQUENCE: 1

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Phe
                325                 330

<210> SEQ ID NO 2
<211> LENGTH: 1342

```
<212> TYPE: PRT
<213> ORGANISM: Homo sapiens
<220> FEATURE:
<221> NAME/KEY: misc_feature
<223> OTHER INFORMATION: Human HER3 Protein Precursor amino acid
      sequence

<400> SEQUENCE: 2

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
```

```
            370                 375                 380
Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                    405                 410                 415

Thr Ile Gly Gly Arg Ser Leu Tyr Asn Arg Gly Phe Ser Leu Leu Ile
                420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
        450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                    485                 490                 495

Gly Lys Val Cys Asp Pro Leu Cys Ser Ser Gly Gly Cys Trp Gly Pro
                500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
530                 535                 540

His Glu Ala Glu Cys Phe Ser Cys His Pro Glu Cys Gln Pro Met Gly
545                 550                 555                 560

Gly Thr Ala Thr Cys Asn Gly Ser Gly Ser Asp Thr Cys Ala Gln Cys
                    565                 570                 575

Ala His Phe Arg Asp Gly Pro His Cys Val Ser Ser Cys Pro His Gly
                580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
        610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                    645                 650                 655

Met Met Leu Gly Gly Thr Phe Leu Tyr Trp Arg Gly Arg Arg Ile Gln
                660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
        690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                    725                 730                 735

Ile Pro Val Cys Ile Lys Val Ile Glu Asp Lys Ser Gly Arg Gln Ser
                740                 745                 750

Phe Gln Ala Val Thr Asp His Met Leu Ala Ile Gly Ser Leu Asp His
            755                 760                 765

Ala His Ile Val Arg Leu Leu Gly Leu Cys Pro Gly Ser Ser Leu Gln
        770                 775                 780

Leu Val Thr Gln Tyr Leu Pro Leu Gly Ser Leu Leu Asp His Val Arg
785                 790                 795                 800
```

-continued

```
Gln His Arg Gly Ala Leu Gly Pro Gln Leu Leu Asn Trp Gly Val
                805                 810                 815
Gln Ile Ala Lys Gly Met Tyr Tyr Leu Glu Glu His Gly Met Val His
                820                 825                 830
Arg Asn Leu Ala Ala Arg Asn Val Leu Leu Lys Ser Pro Ser Gln Val
                835                 840                 845
Gln Val Ala Asp Phe Gly Val Ala Asp Leu Leu Pro Pro Asp Asp Lys
            850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                885                 890                 895
Tyr Gly Val Thr Val Trp Glu Leu Met Thr Phe Gly Ala Glu Pro Tyr
                900                 905                 910
Ala Gly Leu Arg Leu Ala Glu Val Pro Asp Leu Leu Glu Lys Gly Glu
                915                 920                 925
Arg Leu Ala Gln Pro Gln Ile Cys Thr Ile Asp Val Tyr Met Val Met
            930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                965                 970                 975
Val Ile Lys Arg Glu Ser Gly Pro Gly Ile Ala Pro Gly Pro Glu Pro
                980                 985                 990
His Gly Leu Thr Asn Lys Lys Leu Glu Glu Val Glu Leu Glu Pro Glu
                995                 1000                1005
Leu Asp Leu Asp Leu Asp Leu Glu Ala Glu Glu Asp Asn Leu Ala
            1010                1015                1020
Thr Thr Thr Leu Gly Ser Ala Leu Ser Leu Pro Val Gly Thr Leu
            1025                1030                1035
Asn Arg Pro Arg Gly Ser Gln Ser Leu Leu Ser Pro Ser Ser Gly
            1040                1045                1050
Tyr Met Pro Met Asn Gln Gly Asn Leu Gly Gly Ser Cys Gln Glu
            1055                1060                1065
Ser Ala Val Ser Gly Ser Ser Glu Arg Cys Pro Arg Pro Val Ser
            1070                1075                1080
Leu His Pro Met Pro Arg Gly Cys Leu Ala Ser Glu Ser Ser Glu
            1085                1090                1095
Gly His Val Thr Gly Ser Glu Ala Glu Leu Gln Glu Lys Val Ser
            1100                1105                1110
Met Cys Arg Ser Arg Ser Arg Ser Arg Ser Pro Arg Pro Arg Gly
            1115                1120                1125
Asp Ser Ala Tyr His Ser Gln Arg His Ser Leu Leu Thr Pro Val
            1130                1135                1140
Thr Pro Leu Ser Pro Pro Gly Leu Glu Glu Glu Asp Val Asn Gly
            1145                1150                1155
Tyr Val Met Pro Asp Thr His Leu Lys Gly Thr Pro Ser Ser Arg
            1160                1165                1170
Glu Gly Thr Leu Ser Ser Val Gly Leu Ser Ser Val Leu Gly Thr
            1175                1180                1185
Glu Glu Glu Asp Glu Asp Glu Glu Tyr Glu Tyr Met Asn Arg Arg
            1190                1195                1200
```

```
Arg Arg His Ser Pro Pro His Pro Pro Arg Pro Ser  Ser Leu Glu
    1205            1210            1215
Glu Leu Gly Tyr Glu Tyr Met Asp Val Gly Ser Asp  Leu Ser Ala
    1220            1225            1230
Ser Leu Gly Ser Thr Gln Ser Cys Pro Leu His Pro  Val Pro Ile
    1235            1240            1245
Met Pro Thr Ala Gly Thr Thr Pro Asp Glu Asp Tyr  Glu Tyr Met
    1250            1255            1260
Asn Arg Gln Arg Asp Gly Gly Pro Gly Gly Asp  Tyr Ala Ala
    1265            1270            1275
Met Gly Ala Cys Pro Ala Ser Glu Gln Gly Tyr Glu  Glu Met Arg
    1280            1285            1290
Ala Phe Gln Gly Pro Gly His Gln Ala Pro His Val  His Tyr Ala
    1295            1300            1305
Arg Leu Lys Thr Leu Arg Ser Leu Glu Ala Thr Asp  Ser Ala Phe
    1310            1315            1320
Asp Asn Pro Asp Tyr Trp His Ser Arg Leu Phe Pro  Lys Ala Asn
    1325            1330            1335
Ala Gln Arg Thr
    1340

<210> SEQ ID NO 3
<211> LENGTH: 4975
<212> TYPE: DNA
<213> ORGANISM: Homo sapiens
<220> FEATURE:
<221> NAME/KEY: misc_feature
<223> OTHER INFORMATION: Human HER3 mRNA sequence

<400> SEQUENCE: 3
ctctcacaca cacacacccc tccctgcca tccctcccg gactccggct ccggctccga     60
ttgcaatttg caacctccgc tgccgtcgcc gcagcagcca ccaattcgcc agcggttcag    120
gtggctcttg cctcgatgtc ctagcctagg ggccccggg ccggacttgg ctgggctccc    180
ttcaccctct gcggagtcat gagggcgaac gacgctctgc aggtgctggg cttgcttttc    240
agcctggccc gggctccga ggtgggcaac tctcaggcag tgtgtcctgg gactctgaat    300
ggcctgagtg tgaccggcga tgctgagaac caataccaga cactgtacaa gctctacgag    360
aggtgtgagg tggtgatggg gaaccttgag attgtgctca cggacacaa tgccgacctc    420
tccttcctgc agtggattcg agaagtgaca ggctatgtcc tcgtggccat gaatgaattc    480
tctactctac cattgcccaa cctccgcgtg gtgcgaggga cccaggtcta cgatgggaag    540
tttgccatct tcgtcatgtt gaactataac accaactcca gccacgctct cgccagctc    600
cgcttgactc agctcaccga gattctgtca ggggtgttt atattgagaa gaacgataag    660
ctttgtcaca tggacacaat tgactggagg gacatcgtga gggaccgaga tgctgagata    720
gtggtgaagg acaatggcag aagctgtccc cctgtcatg aggtttgcaa ggggcgatgc    780
tggggtcctg atcagaaga ctgccagaca ttgaccaaga ccatctgtgc tcctcagtgt    840
aatggtcact gctttgggcc caacccccaac cagtgctgcc atgatgagtg tgccgggggc    900
tgctcaggcc ctcaggacac agactgcttt gcctgccggc acttcaatga cagtggagcc    960
tgtgtacctc gctgtccaca gcctcttgtc tacaacaagc taactttcca gctggaaccc   1020
aatccccaca ccaagtatca gtatggagga gtttgtgtag ccagctgtcc ccataacttt   1080
gtggtggatc aaacatcctg tgtcagggcc tgtcctcctg acaagatgga agtagataaa   1140
```

```
aatgggctca agatgtgtga gccttgtggg ggactatgtc ccaaagcctg tgagggaaca    1200
ggctctggga gccgcttcca gactgtggac tcgagcaaca ttgatggatt tgtgaactgc    1260
accaagatcc tgggcaacct ggactttctg atcaccggcc tcaatggaga ccctggcac    1320 aagatccctg ccctggaccc agagaagctc aatgtcttcc ggacagtacg ggagatcaca    1380
ggttacctga acatccagtc ctggccgccc cacatgcaca acttcagtgt tttttccaat    1440
ttgacaacca ttggaggcag aagcctctac aaccggggct tctcattgtt gatcatgaag    1500
aacttgaatg tcacatctct gggcttccga tccctgaagg aaattagtgc tgggcgtatc    1560
tatataagtg ccaataggca gctctgctac caccactctt tgaactggac caaggtgctt    1620
cgggggccta cggaagagcg actagacatc aagcataatc ggccgcgcag agactgcgtg    1680
gcagagggca aagtgtgtga cccactgtgc tcctctgggg gatgctgggg cccaggccct    1740
ggtcagtgct tgtcctgtcg aaattatagc cgaggaggtg tctgtgtgac ccactgcaac    1800
tttctgaatg gggagcctcg agaatttgcc catgaggccg aatgcttctc ctgccacccg    1860
gaatgccaac ccatgggggg cactgccaca tgcaatggct cgggctctga tacttgtgct    1920
caatgtgccc atttcgaga tgggccccac tgtgtgagca gctgccccca tggagtccta    1980
ggtgccaagg gcccaatcta caagtaccca gatgttcaga atgaatgtcg gccctgccat    2040
gagaactgca cccaggggtg taaaggacca gagcttcaag actgtttagg acaaacactg    2100
gtgctgatcg gcaaaaccca tctgacaatg gctttgacag tgatagcagg attggtagtg    2160 atttcatga tgctgggcgg cactttctc tactggcgtg ggcgccggat tcagaataaa    2220
agggctatga ggcgatactt ggaacggggt gagagcatag agcctctgga ccccagtgag    2280
aaggctaaca agtcttggc cagaatcttc aaagagacag agctaaggaa gcttaaagtg    2340
cttggctcgg gtgtctttgg aactgtgcac aaaggagtgt ggatccctga gggtgaatca    2400
atcaagattc cagtctgcat aaagtcatt gaggacaaga gtggacggca gagttttcaa    2460
gctgtgacag atcatatgct ggccattggc agcctggacc atgcccacat tgtaaggctg    2520
ctgggactat gcccagggtc atctctgcag cttgtcactc aatatttgcc tctgggttct    2580
ctgctggatc atgtgagaca acccggggg gcactgggc acagctgct gctcaactgg    2640 ggagtacaaa ttgccaaggg aatgtactac cttgaggaac atggtatggt gcatagaaac    2700
ctggctgccc gaaacgtgct actcaagtca cccagtcagg ttcaggtggc agattttggt    2760
gtggctgacc tgctgcctcc tgatgataag cagctgctat acagtgaggc caagactcca    2820
attaagtgga tggcccttga gagtatccac tttgggaaat acacacacca gagtgatgtc    2880
tggagctatg gtgtgacagt ttgggagttg atgaccttcg gggcagagcc ctatgcaggg    2940
ctacgattgg ctgaagtacc agacctgcta gagaagggg agcggttggc acagccccag    3000
atctgcacaa ttgatgtcta catggtgatg gtcaagtgtt ggatgattga tgagaacatt    3060
cgcccaacct ttaaagaact agccaatgag ttcaccagga tggcccgaga cccaccacgg    3120
tatctggtca taaagagaga gagtgggcct ggaatagccc tgggccaga gcccatggt    3180 ctgacaaaca agaagctaga ggaagtagag ctggagccag aactagacct agacctagac    3240
ttggaagcag aggaggacaa cctggcaacc accacactgg gctccgccct cagcctacca    3300
gttggaacac ttaatcggcc acgtgggagc cagagccttt taagtccatc atctggatac    3360
atgcccatga accagggtaa tcttgggggg tcttgccagg agtctgcagt ttctgggagc    3420
agtgaacggt gccccgtcc agtctctcta cacccaatgc cacggggatg cctgcatca    3480 gagtcatcag aggggcatgt aacaggctct gaggctgagc tccaggagaa agtgtcaatg    3540
```

```
tgtagaagcc ggagcaggag ccggagccca cggccacgcg gagatagcgc ctaccattcc    3600
cagcgccaca gtctgctgac tcctgttacc ccactctccc cacccgggtt agaggaagag    3660
gatgtcaacg gttatgtcat gccagataca cacctcaaag gtactccctc ctcccgggaa    3720
ggcacccttt cttcagtggg tctcagttct gtcctgggta ctgaagaaga agatgaagat    3780
gaggagtatg aatacatgaa ccggaggaga aggcacagtc cacctcatcc ccctaggcca    3840
agttcccttg aggagctggg ttatgagtac atggatgtgg ggtcagacct cagtgcctct    3900
ctgggcagca cacagagttg cccactccac cctgtaccca tcatgcccac tgcaggcaca    3960
actccagatg aagactatga atatatgaat cggcaacgag atggaggtgg tcctgggggt    4020
gattatgcag ccatggggc ctgcccagca tctgagcaag ggtatgaaga gatgagagct    4080
```
(the above partial row; continuing as printed)

```
tttcaggggc ctggacatca ggccccccat gtccattatg cccgcctaaa aactctacgt    4140
agcttagagg ctacagactc tgcctttgat aaccctgatt actggcatag caggcttttc    4200
cccaaggcta atgcccagag aacgtaactc ctgctccctg tggcactcag ggagcattta    4260
atggcagcta gtgcctttag agggtaccgt cttctcccta ttccctctct ctcccaggtc    4320
ccagcccctt ttccccagtc ccagacaatt ccattcaatc tttggaggct tttaaacatt    4380
ttgacacaaa attcttatgg tatgtagcca gctgtgcact ttcttctctt tcccaacccc    4440
aggaaaggtt ttccttattt tgtgtgcttt cccagtccca ttcctcagct tcttcacagg    4500
cactcctgga gatatgaagg attactctcc atatcccttc ctctcaggct cttgactact    4560
tggaactagg ctcttatgtg tgcctttgtt tccatcaga ctgtcaagaa gaggaaaggg    4620
aggaaaccta gcagaggaaa gtgtaatttt ggtttatgac tcttaacccc ctagaaagac    4680
agaagcttaa aatctgtgaa gaaagaggtt aggagtagaa attgattact atcataattc    4740
agcacttaac tatgagccag gcatcatact aaacttcacc tacattatct cacttagtcc    4800
tttatcatcc ttaaaacaat tctgtgacat acatattatc tcattttaca caaagggaag    4860
tcgggcatgg tggctcatgc ctgtaatctc agcactttgg gaggctgagg cagaaggatt    4920
acctgaggca aggagtttga gaccagctta gccaacatag taagacccc atctc         4975
```

<210> SEQ ID NO 4
<211> LENGTH: 30237
<212> TYPE: DNA
<213> ORGANISM: Homo sapiens
<220> FEATURE:
<221> NAME/KEY: misc_feature
<223> OTHER INFORMATION: Human HER3 DNA sequence

<400> SEQUENCE: 4

```
tttttttatt gataattctt gggtgtttct cacagagggg gatttggcag ggtcatggga     60
caatagtgga gggaaggtca gcagataaac aagtgaacaa aggtctctgg ttttcctagg    120
cagaggaccc tgcggccttc cgcagtgttt gtgtccctga ttacttgaga ttggggagtg    180
gtgatgactc ttaatgagca tgctgccttc aagcatctgt ttaacaaagc acatcttgca    240
ccgcccttaa tccatttaac cctgagtgga cacagcacat gtttcagaga gcacagggtt    300
gggggtaagg tcacagatca acaggatccc aaggcagaag aattttttctt agtgcagaac    360 aaaatgaaaa gtctcccatg tctacttctt tctacacaga cacggcaacc atccgatttc    420
tcaatctttt ccccaccttt cccgcctttc tattccacaa agccgccatt gtcatcctgg    480
cccgttctca atgagctgtt gggtacacct cccagacggg gtggtggccg ggcagaggtg    540
cccctcacct cccagacggg gcggctggcc gggcgggggg ctgaccccccc cacctccctc    600
```

```
ccggacgggg cggctggccg ggcggggggc tgaccccca acctccctcc ccgacggggc      660
ggctggccgg gcggggggct gaccccccca cctccctcct ggacggggcg gctgatcggg      720
cgaggggctg accccccat ctccctcccg gatggggtgg ctgccgggcg gagactctcc       780
tcacttccca gatggggtgg ctgccgggcg gagaggctcc tcacttctca gacggggcag      840
ctgccggacg gagggctcc tcacttctca gacggggtgg ttgccaggca gagggtctcc       900
tcacttctca gacggggcgg ccgagcagag acgctcttca cctcccagac ggggtcgctg      960
ccgggcagag gcgctcctca tatcccagat ggggcggcgg ggcagaggcg ctccccacat     1020
ctcagacaat gggcggccgg gcagagacgc tcctcacttc ctagatgtga tggcggccgg     1080
gaagaggcgc tcctcacttc ctagatggga tggcggcagg gcggagacgc tcctcacttt     1140
ccagactggg cagccaggca gagggctcc tcacatccca gacgatgggc ggccaggcag      1200
agacactcct cacttcccag acggggtggc ggccgggcag aggctgcaat ctcagcactt     1260
tgggaggcca aggcaggcgg ctgggaggtg taggttgtag tgagccgaga tcacgccact     1320
gcactccagc ctgggcacca ttgagcactg agtgaacgag actccgtctg caatcccggc     1380
acctcgggag gccgaggctg gcggatcact cgcggttagg ggctggagac cggcccggcc     1440
aacacagcga aaccccgtct ccaccaaaac cagtcaggcg tggcggcgcg tgcctgcaat     1500
cgcaggcact cggcaggctg aggcaggaga atcaggcagg gaggttgcag tgagccgaga     1560
tggcagcagt acagtccagc ttcggctccg catgagaggg agaccgtgga aagagaggga     1620
gaccgtgggg agagggagag ggggagggg aggggaggg ggagggacca atcaacagtc       1680
ttataagtag atacaacagt gtataaacaa ggaaaccaag gaagattttt ctccttcaga     1740
actcggaccc tgaataccag gttgagctgg agctgagtga gtaataaaat gaaaggccct     1800
ttaatgtggg ggagggtagg taggagtgga gacccttaag tagtatcagc actgttgtct     1860
gatgggagtg tgaatctgaa cacatgaagc tccagtctca gtagaacagt aagaaatcct     1920
aagtaaggcc aggcatggtt cacatctgaa atcctaacaa tttgggtaaa ctgaggtgga     1980
aggattgcag aggccaggag ttcaagacca gcttgggcaa catagccaga ccccaccc      2040 cacccccgca tctccatatc atacaaaaat aataaagaaa tcctaggtaa ggccagatgg     2100
taaggccagg tgtggtggct catgcctgta atcccagcac tttgggaggc cgaggtgggt     2160
ggattgccca aggtcaggag ttcaagacca gcttggtcaa cacagtgaaa ccccgtctct     2220
actaaaaata caaaaattag ctaggtgttg tggcaggcac ctgtaatctc aactactcag     2280
gaggctgagg caggagaata gcttgaaccc aagaggcaga ggttgcagtg agccaagatc     2340
gagccattgc actccagcct gggcaccaaa agcgaaactc aggagaatgc cttgaaccca     2400
ggaggcagag gttgcagtga gctgagatca cgccattgca ctccagcctg ggtgacagag     2460
cgagactcca tctcaaaaac aaacaaacaa ataaacaaag tagccagaca ttttggtgcc     2520
cacctgtaga ctcagttact agggaggctg aagtgggaga atcacctgag cctgggaagt     2580
tgaggctgct gtgagccatg attgcaccac tgcactccag cctgggtgac agaggagat     2640 cctgtctcaa aaaaggaaa aaaagccagg tgtggtggct cacacctgta atcccagcac     2700
tttgggaggc tgaggtgggt ggatcacctg aggtcaggaa ttagagacta gtctggccat     2760
cacagtgaaa ccccatctct actaaaaata caaaaaatta gccgggcttg gtggcgcacg     2820
ccttgtagcc ccagctactt ggaagcctga ggcaggagaa tcacttgaac tcagtagtga     2880
gctgagatca ggccactgca ctccagcctg ggtgacagaa acagaacaag attccgtgtc     2940
```

```
aaaaaaaaaa aagcaacaga ccagaaggcc atgaggtcaa acaaacaat gttttgtttt      3000 tgttttgaga tggcgtctca ctctgtcgcc caagctggag tgcagtgatg caatctcagc      3060
tcactgcaac ctccacctcc cgggttcaag cgattctcct gcctcagtct cctaagtagc      3120
tgggattaca ggtgcccacc atcatgccca gctaattttt gtatttttag tagagacggt      3180
gtttcactat gttgactagg ctggtctcga actcctgacc tcaagtgatc tgcccgcctc      3240
ggcctcccaa agtgctggga ttacaggcat gagccaccgc gcccagccga atgttttgtt      3300
ttttaagatg gaagatatcc cagcactttg gcaggctgaa gcaggtggat cattccagct      3360
tgggcaacaa gagcgaaact ctgtctcaaa aaaaaaaaa aagaaaagaa aaaaaagag      3420 agaaagaaac cctaggtaaa agtctgagcc ccacctccca atcacctgat cacctcaacc      3480
actgtcacca ggtggatgac cttggagagg tcacacactt ctagttctgt aaaatgggga      3540
gttatattgc ctaaatcata taattttat gttaagtgac acattctcta aggcactaag      3600
tttgaggaca tactttgtaa atgaaatgat atatggaaat gtttgtatat gttaatggtt      3660
ttgttgttgc tattattatt atgactacta tacacatggt ctggagaaag ccaacctccc      3720
caaagcggag attctccagt agagaacagg ccctctaggt tgcatatcaa tagggagcat      3780
gtttaaggaa tgttagccgg tagtctttgc taggtgtgag gggtgaaatt tttctttatc      3840
aaggctcaac tgttttcgaa gtcttcaggc ttgaagttct ggagaaaaca actaggctct      3900
ccgggcgaga tcccgaatac cagtttaagg gatttgaaat gcaaggccgt ctgggactcc      3960
actgccacgg atgggcacca ggcggcgccg gtcggatccg tcccgggact agcagggctt      4020
tgggcagcaa cccgcaggga gcccgaccgc ctctggccag gtccgggcag ctggtggggg      4080
aggttccaga ggtccacgcc attcgtggac gcagtctcta gtgtcctctc cgcgtcccac      4140
ttcactgccc catccccttt cctgcgagag cctggacttg gaaggcacct gggagggtgt      4200
aagcgccttg gtgtgtgccc atctgggtcc ccagaagagc ggcgggaact gcggccgccc      4260
ggacggtgcg gccagactcc agtgtggaag gggaggcagc tgttctccca ggcggccgtg      4320
gggggcagca gaggggacgg cgacaggtgc gggagcccct cccggggtag aagtggaaag      4380
gcgggctccg gggtctgttc ccaggctgga aaccacccc gccccccatc caaatccccg      4440
ggagaggccc ggccggcgcc gggtctggag gaggaagcgg ccagagacag tgcaatttca      4500
cgcggtctct gtggctcggg ttcctgggct ggtggatga attatggggt ttcgagtctg      4560
ggagaaactg aggtggcctg gacgtgaggc aaaaaacacc ctccccctca aaaacacaca      4620
gagagaaata ttcacattct gagagaaaat ccaccaagtg aaccaaccgg ctaggggagt      4680
tgagtgattt ggttaatggg cgaggccaac tttcaggggg cagggctttg gagagctttc      4740
cactccctca ttcattaccc ttccctggat ctgggggctt tcggaatctc gacctcccct      4800
tggcctatct cctgcagaaa aattagggtg agccccatcc tcgatctgct ccgccaagtt      4860 gcggaccgc gggcgtggc acgctcgggg caggcggtcc gaggctccgc aatccctact      4920
ccagcctcgc gcgggagggg gcgcggccgt gactcacccc cttccctctg cgttcctccc      4980
tccctctctc tctctctctc acacacacac acccctcccc tgccatccct cccggactc      5040 cggctccggc tccgattgca atttgcaacc tccgctgccg tcgccgcagc agccaccaat      5100
tcgccagcgg ttcaggtggc tcttgcctcg atgtcctagc ctaggggccc ccgggccgga      5160
cttggctggg ctcccttcac cctctgcgga gtcatgaggg cgaacgacgc tctgcaggtg      5220
ctgggcttgc ttttcagcct ggccggggc tccgaggtgg gcaactctca ggcaggtaag      5280
tggcgcgaga gcaccggcgg gctcggcacc tgggagccgg aacccagtgc gcgcagcctc      5340
```

```
ggagggtatg ggcacggtct caggcggcgc ggggttgtgg gtgctgcccc cggtttgcca    5400
ggaccacctg ggagaggggc ggtcaggctc gggttatcgg cgtggtccgg ccagggcgg     5460
cattccggga ccctcacgcc acccttctcc agagcgtcgc cgaccctcta attggtctcc    5520
ccagaagagg ctgaggccga aacagtagtt cacacttctg aggggccctg caggaggggg    5580
agcagggaac ttcattctgt aaacaggagg tgcttggagg tgggggcctt ggcgggaagg    5640
gtctcggttt gctcgccaac cccctgcccc cacccgcgc cgatttcagc taccccctagt    5700
ttcgttgttt tgccgacagg gcggagctac agaaggttgg aggggttgt tgttctctgg     5760
tgttggaaaa acaggagcgg cacctcctct tccgtgagtg agcctgccct ggggaggtct    5820
gagattaacc agagggccaa gttcaggtga catcaggcag gaggcccaac agaggctggc    5880
gccccctttc ctcagtatag cagagcttaa gcaacatctc tttgtcaaga cccaggtcaa    5940
cacaactcat atttattgag catctactat acacaaggcc ctgggccagg agctgtaagg    6000
gcaaggatgt ccagcctctg gtcttttctc tccccaacct gaggatcaag agggcacctc    6060
tgctactttc taagcctcct gccttgggga gtccttcctg ggctcagctt gtgcctcccg    6120
cccccatttt gcttattgtc tgacactgtc tctaggaccc tagacagagc cccggattgc    6180
tcttctccag tcctccccg actcccatgc tatctgagcc cacccctttg gggtgtctct     6240
gggaccgtgg acacctgagg actgaagttc tgtggatctc ctcccctccc ctcagatctc    6300
agcttggggt ttggcacagc cagggcccct tccccagtgt gggagtggaa gaaaccacct    6360
gtgcttccct cacagttgct gggcctaaat ttagatcctg ggattttag atgtgaacac     6420
tcccagctgg tggagggggg tggtctgggg actggcgtgg gagggagcag tggagtgact    6480
gtataactgt cccatccaga ctcctgcaat cttcacccag aaaccagga gtaccagagt     6540
ctggccaccc tccctgggga ggcaggaggc aggcatggtt gggtctcttt accctttatc    6600
tgggtcctgc agcctctggg catccggccc tgtctcagtc cttctatagc ccctttgtcc    6660
tggctgtgat gggggtgggg gatgttggag gggaggcctc tggttgagga ggggctggag    6720
attctggctc tatcccaccc ctagtgctct ctaccaaagg agggcctgtg acactgcccc    6780
tccctatgct cccggttcct gggtacagca gggattttta tgattccctt ccctgcccc    6840
gctccccaag ctgcctagct cctccccaga ggtgttgttt gtgctcccctt cctgcccagg   6900
cccttttgccc cctgtttgtg taatatggac tttaccctca gggtagcagg gaactgggct   6960
acctctaaca ctgtagcctt ccaagcacag acacaaagtc tgcacaaaca cttatgggca    7020
cgtgggatag atggggccac ctgaaatact tcctgcaagg aaacccaact atagattcct    7080
gagccagcag gaccaatgtg tacgtgttcg tgtgtacatt gtgtgtgtat gtgtgtgccc    7140
acactactac ttccctgtgc agaaagcttg gctcctccct tatctgggga gaagtgttgg    7200
cactataact tgggaaaggg ggtatcctgc caggaagggg attggggtgg ggctgttcca    7260
gaaatgacta accttcctag tctctttcat ttcaacccaa ggaccctgga gttcccagct    7320
cctctggaac tagctctctt tgctgggact agccaaccct catggggagt gataaggagc    7380
cctccaaggt caagaagtca gactaggggt gtatgttata ggagggattg gggcctcacc    7440
agtctccctc cctccattcc cactgttgcc tcccactgag ctaccaccgc ctcagggaag    7500
ggtggctgga acaggtggta tctacccccct actccccacc ccacacatgg tctttccctg   7560
aaccagagga aagagactgg ggtagggctt cagagtccag gacttcccat agcccgttgt    7620
ccaccacatt tgcaaagaag agtgaactcc caaggctgac atgccatgta cctctagtct    7680
```

```
aggctctccc ctagtgtggg tgaggattgc catggtgaaa ggcttttca tgaacctctt      7740
ctaacaatga aattgtgtgg aggctcaata tggggcatct gctactatct ctctccaggt      7800
tcctctgtat ttgctgaaaa atactctagg gctggaaagt gatgctgagg ttgctagagt      7860
gtgttgggat gggggagaga gtgagaagga aaccctgagt ttaggaaggc ggggaggcaa      7920
ctagctcctt atctttcagc tttaaagaca aagctcccat tgaccccccc tcacccagc      7980
actgccagag ctcccccctc tactgaggtc acttgtctga gcccaaggct tgagggtgga      8040
ggggagtgct gctgaggacg gggtgtctag ggacagggtg gggcagcccc cctcctggat      8100
agaatcgcct cattgtgggc tggactgtgg ccccaggcac tgcccccacc ctctgccccc      8160
atcccaccct cagtagacac aatagggct gtgtactagt cccaaagaga tatttattcc      8220
aggacctaga gagaggcagg atgagggtag agaagtgagt gccctagttg aggggggaga      8280
ggagggtaat caaagttgcg gccttttcct aacttctctt ttctagggag agaaacaaat      8340
tccctgtctt ccttctcagt taaccccctta gtacccaaaa gaagcacaga ggggtcccag      8400
gttgaaaaag gaaatctttt caccttccca ttcatggaat ggtaagggga ttctgagaag      8460
agagaaagct ctcaggccac tacagcttct gcctatcgct tgtgggaggg ttggaggcaa      8520
atgccatctg atcctgtcta atgtaactgg aagagggcaa ccaaggggt gatctttggg      8580
gatggcagat gggctgagaa tttgtgtcca gccctcagcc actcttccct ctgctttgaa      8640
cagtgtgtcc tgggactctg aatggcctga gtgtgaccgg cgatgctgag aaccaatacc      8700
agacactgta caagctctac gagaggtgtg aggtggtgat ggggaacctt gagattgtgc      8760
tcacgggaca caatgccgac ctctccttcc tgcaggttag tgagcccacc ctccttcctc      8820
aacctgctcc tctttattct cccctagaac cctccttcct tcttcagggc taccttctgc      8880
tggagttcac ccttcctaag actcaggagt tcctaagatt caaaaccgtg tatttatggg      8940
gacagtggct gtcatctggg acctatggtc tcactgttgt agccagggat atataggggg      9000
cagggtcagg ggcaggtggt gttctgtgga tagtgcaagg tcagcaggga ctagtgcaga      9060
gagaaacctg aggaccaaga ggttacctgg ggagatgagg aagggccct actggtatga      9120
ggcactttga ggagaaagct gcctgtcttc actcccagaa gtgacacagc agtgtgacac      9180
agtctactcc ctactcccaa ataggaatta gcaagagtta aggccaggtg cagtggctca      9240
tgcctgtaat cccagcactt tgggaggcca aggaaggcag atcacttgag gtcaggagtt      9300
caagaccagc ctgggcaatg tggtgaaacg ctgtctctac aaaaatacaa aaattagctg      9360
ggtatggtgg catgcacctg tagtcccagc tacttgagg gctgaggtgg gaggattgct      9420
tgagcccagg agtttgacgc tgcagtgagc gagattgtgc cactcgtaac agagcgagac      9480
cctgtctcac caaaaaaaaa aaaaaggcc aagctcggat cacctgaggt caggagttcg      9540
agaccagcct gaccaacatg gaaaaccac atctctacta aaaatacaaa attagccagg      9600
tgtagtggca catgcctgta atcccagcta cttgggaggc tgcggcagga gaattgcttg      9660
aacccgggag gtggaggttg tggtgagcca agatcgcact attgtactcc agcctgggca      9720
acaagagcgt aactccgtct caaatttaa aaaaagaaa aaagaaagg aaagaaagaa      9780
ggaagaatta aaacagttaa agagtctta atgcctgaag gaggagagga gattgagatt      9840
attttgccct gttgtctctc tcatttacat aatctgctct gtcacagtgg attcgagaag      9900
tgacaggcta tgtcctcgtg gccatgaatg aattctctac tctaccattg cccaacctcc      9960
gcgtggtgcg agggacccag gtctacgatg ggaagtttgc catcttcgtc atgttgaact     10020
ataacaccaa ctccagccac gctctgcgcc agctccgctt gactcagctc accggtcagt     10080
```

```
tcccgatggt tccttctggc ctcacccctc agccagccca agactggtac ctccttgatg    10140
atgacccaag actgctcact ctaagtgcct cttccaaggt gcctgtcacc ttggccgctg    10200
tctaaaggtc cattgctccc taagcaatag agggccccca gtaggggag ctagggcat     10260
ctgctccagg gaaaggaacc ctgtgtcctt gtggggctgg agtcagagct ggatctgtta    10320
accgtttttc taatttcaaa gtacagtgta ccggaggcca ggcctgatgg cttacacctg    10380
taatcccagc attttgggag gccaaggagg gcagatcact tgagatcagg agtttgagac    10440
cagcctggcc aacatggcga aaccctgtct ctactaaaaa tacaaaaaaa taaaataaaa    10500
taaaaaatta gctggctata gtggtgcgca cctgtaatcc cagctgttca tgaggctgag    10560
gcaggagact cgcttgaacc tgggaggtgg aggttgcagt gagctgagat tgcaccactg    10620
cactctagcg taagtgacag tgagactccg tctcaaaaaa aaaaaaaaaa aaaaaaaaaa    10680
gcctgggcgc ggtggctcac gcctgtaatc ccagcacttt gggaggccaa ggcaggtgga    10740
tcacaaggtc aggagatcga gaccatcctg gctaacacgg tgaaacccg tctctactaa     10800
aaatacaaaa aattagccag gtgtggtggc gggcgcctgt agtccgagct actcgggagg    10860
ctgaggcagg agaatggcgt gaacccggga ggcggagctt gcagtgagcc aagattgcac    10920
cactgcactc cagcctgggc gacagagcga gactccaaaa aaaaaaaaaa aaaaaaaaac    10980
caaagtacag tatacctgga tgtccctcct ccctaggaa ttctaccttt actctcctaa     11040
accaaacccc tatgagctgg aggaatatag gggttaaaaa ccacctgtcc atcttctgct    11100
tctccatgtc ccagtcagtt ggaaaacata tgggcagggc ttgggggagg gaatgttgag    11160
tcagaaatct ctccctctct cccttcccct ccccactag ctaaaccgga tctggacagg     11220
tgactgagga ggcaggagtt tcttttggcc tgactcctca tcttataaag ggagtcttct    11280
ctgcagctta gatttaattg gacctatctg tctgcctcat tctcccactc ctgagtctca    11340
ggtgtccttt tggatgggtg gagaggtaag gaagaggcgt tccgctgcgg cccttaaccc    11400
tgtcacttct ttccctacct cagagattct gtcagggggt gtttatattg agaagaacga    11460
taagctttgt cacatggaca caattgactg gagggacatc gtgagggacc agatgctga    11520
gatagtggtg aaggacaatg gcagaagctg taagtggccg tgatcaagat tgctccccag    11580
tcccaccaaa ccagagtgac tcccttcttt ccatcatcct tacattcctg atctgaaccc    11640
gcctccccag tgaacaaaca cctcaggtcc ctgactcagc agcccaccag ggcagaccat    11700
tccagtctcc tggaatctaa accacagagg aggtgtttca agaaaaggag caggccgagc    11760
atggtggctc atgcctataa tcctggcact ttgggaagcc aaggtgggag gatcgcttga    11820
gcccaggagt ccaagaccag cctgagtaac atagcaaaaa atctacaaaa aattaaaaaa    11880
atcagacagg cgtagtggct cgcacctgta atcccggcta ctcaggaggc tgaggcagag    11940
gattgcttga gcccaggagg ctgcagctgc agtgagctgt gattgtgcca ttgtactcta    12000
gcctgggcaa cagagtgaga ccctgtctca aaaaaaaaaa aaaaaaatcc ctgagtacta    12060
agcagggaag ccagatcttt agactccaca tctgttactc gttccactag aatatactcc    12120
catttccttg gagcccacct tcccctgacc attcacatgc atatattcct gcatatattc    12180
agtttgccca ggaggaacta agttcctggg ttggactag gactaaggtt ggcatttgcc     12240
ccagtccctc cccttcagct gcccagtggg tggtgtggag gcgtggccgc gccccttgtt    12300
gacaggtcca cttgagccca gccctgctct ccaaggcag ggagggacac agccctggct     12360
ttttgcttcc cgggattgag gtgcctgtgt actgacatca taccccgttg attaaaacaa    12420
```

```
gcctttctta gccctgatgg cccctttgtgt tgccttcctt cccaaccagg tcccccctgt  12480
catgaggttt gcaaggggcg atgctggggt cctggatcag aagactgcca gacatgtggg  12540
tttgaaattc cctccaaaaa cttcactcat acgctttcat atcccttcct ccccaagcct  12600
gggtcaacac tgtgggggag gcatgagcag tggcctcaga attcagtcct aggagcccta  12660
acagccatgc tttctctcct tccatagtga ccaagaccat ctgtgctcct cagtgtaatg  12720
gtcactgctt tgggcccaac cccaaccagt gctgccatga tgagtgtgcc ggggctgct   12780 caggccctca ggacacagac tgctttgtat gtacccttc cattgcctgg gttctgaaat   12840
tgggatgtgg cctttgagga ggaggtaggg gtacacacgt aacataaatc tgatgagcct  12900 cctttttttcc caggcctgcc ggcacttcaa tgacagtgga gcctgtgtac ctcgctgtcc  12960
acagcctctt gtctacaaca agctaacttt ccagctggaa cccaatcccc acaccaagta  13020
tcagtatgga ggagtttgtg tagccagctg tccccgtaag tgtctgaggg gaaggaacaa  13080
tgatcaacaa tagtagatcc aagattttag acaaaattgt ggaagggaaa aagaatccag  13140
ttggtgataa atagggagat tggtgaatgg ttatgatcat ctaaccactc cagtgagtga  13200
cccttacgtc cagtcctccc atgacttcag ctatcaccct tacttctgct ccttgtagca  13260
acaaatagtg aagagacttt tgaatctata gggcagcact taagggatct agggtggcag  13320
atggggacaa atccagtgca gagctggagg gagcctaggc ccagagcaag ggttccattg  13380
gtagctggtg atgttcctcc ctcatctcta atggtgtcct cctcctcttc cctagataac  13440
tttgtggtgg atcaaacatc ctgtgtcagg gcctgtcctc ctgacaagat ggaagtagat  13500
aaaaatgggc tcaagatgtg tgagccttgt gggggactat gtcccaaagg tgggtaggag  13560
atggtaagaa gttgtaaaga gacagccttt cctctgagcc tgcgcagacc accccactg   13620 aacctctctt acatttgcag cctgtgaggg aacaggctct gggagccgct tccagactgt  13680
ggactcgagc aacattgatg gatttgtgaa ctgcaccaag atcctgggca acctggactt  13740
tctgatcacc ggcctcaatg ggttagagat cctgccttcc ctccttagac cccagcccac  13800
gcacccctca cagttcattt cattggccaa aactttccta tgtggagctg actaggaatc  13860
aaagtcataa aattctagcc tgttacaaag gacctgaaag aatgcttaac acatcctcca  13920
tccaggcctt cggtcccctc aggaacatct ttgagcaatt caatatcgcc ctgccaagga  13980
acaagggaca ggaacaacat atcctccttc ttaaagtttt cttttttatt cttttttctt  14040 tttttgagata gggtcttgct ctgtcaccta ggctggagtg cagtggcgtg atctcgactc  14100
actgtagcct cgacctcctg ggctcaagtg atcccaagta gctgggacta taggcacaca  14160
ccatcatact tgactaattt ttttgtattt ttttgtagag acagggtctt gctatgttgc  14220
ccaggctgat ctcgaactcc tgtgctcaag caatcctccc atcttggcct cccaaagtgc  14280
tagggatcac agcacccaac ctccttctta aagttttgta aaagttcttc cttagatttg  14340
gataaaaatc tgtctccagg ctgggcccgg tggctcatgc ctataatccc agcactttgg  14400
gaggccgagg tgggcggatt acgaggtcag atcgagacca tcctggctaa catggtgaaa  14460
tgccatctct actaaaaaca caaaaattag ctgggtgtgg tggtgcacat gcctgtaatc  14520
ccagctactc aggaggctga ggcacgagaa tcacttgaac ccaggaggcg gaaattgcag  14580
tgaaccgaga ttacaccacc gcactccagc ctggcgacag agcgagactc tttctcaaaa  14640
aaaaaaaaga aaagaaaaga aaattctgtc tccccatgac ttttagctgt tttcactcat  14700
tctgctcctt ggagcaaaaa gaacaaaggg actttctagt ctataggaca gcatttaaaa  14760
tgtgtgtgtg tgtgtaaaaa aaacccacta tgaccacctg ttttttttttt tcctttaatt  14820
```

```
ttttattttg acataatttt agatctacac taaagttgca agaatggtat aaaattcccc   14880
atatactttt tttttttttt taagacaaag tctcactctg ttccccaggc tagagtgcag   14940
tggtgcaatc ttggctcact gcaacctccg cctcctctgc ctcccgggtt caagcaattc   15000
tcctgcctca gtctcctgag tagctggaat tataggtgtg tgccatcatg cccggctaat   15060
ttttgtattt ttagtagaga cagggtttca ccatgtaggc caggctggtc tcgaactcct   15120
gacctcaagt gatccacccg ccccagcttc ccaaagtgtt gggattacaa gtgtgagcca   15180
ccgcgtctgg cccccatac actcttttac ccagatcctc caaatgttaa cataccacat   15240
atggccgggc acagtggctc atgcctataa tcccagcact ttgggaggct gaggcaggtg   15300
gatcactagg tgtggatcac gaggtcaaga gattgagacc atcctggcca catggtgaa    15360 acctcatctc tactaaaaat acaaaaatta gctgggcgtg tggtgtgcg cctgtagtcc    15420 cagttactca ggaggctgag gcaggagaat agcttgaacc tggcaggcag aggttgcagt   15480
gagccgagat cgcggcactg cactccagcc tggtgaaaga gcgagactct gtcccccgcc   15540
aaaaaaaata ccacatacgc tttatcactt ctctctctct ctgtctctct ctacacacac   15600
acacacacac acaaaacaca tgctattgtt tttctggacc acgtgagggt aaattttcac   15660
acatggttct ttcttacccc tgttatattt cagcgtatat tccttaaaaa taatatttc    15720 ttacataacc acagcatagt tgtttgaatc ggaaaattaa cattaacaca aaatattatc   15780
taagctacag accttattca gatttcacta attgtcctcc taaggtttgg gatcatacat   15840
tacattcagt tatcgtggca cttcaatctc ctttataaca gctcctcagg ttttgtttat   15900
ctttcatgat attcttgatg agtatagatt aggtaatggg cagcatgttc ttcagtttgg   15960
attagtttga tgtgtcctca tgattagatt caagttttg tagttttttt ttgagacaag    16020
gtctggctct attcccagg ctggaataca gtggcatgat ctcagctcac tgcaacctct    16080
gcctcccgtg ctcaagcgag cacctcagcc ccctgagtag ctgggattac aggtgcatgc   16140
caccatgctt ggctaatttt atatatatat atatatatat atatataa ataatatata     16200 taaatataaa tatatatata taaataatat atataaatat atataaacat aaatattata   16260
tactatttat atatttatat atgtgtgtgt atatatatat atatttttt tttttttga     16320 gacggagtct cgctcttgtt gcccaggctg gagtgcagtg gcgtgatctc agctcacgca   16380
acctccacct ctcaggttca agccattctc tatagagaca gggttgcacc atgttgtcca   16440
ggatggtctc gaactcatga gctcaagtga tcctcctgtc tcagcctccc aaagtgctgg   16500
gattataggc atgcgccgct gccaggctgg agtttgataa gaacaccaca gaggctgtga   16560
gctcagggca tcctattgag gatgtacgtg atgttgattt gtcccagcac tcacaatgat   16620
gtctctggtc acttagttaa ggtgatatct gtcaggtttt tctactgtaa agttactatt   16680
tttccattca caattaatga atgtcttggg ataattgcct gaatcaatta ttgttatgat   16740
agttgccaaa tgataatttt ctaattccat tattccttct gcatttgttt gttggcattc   16800
tactgttagg aagagtcttt ccagctgagc acagtggctt atgcctgtaa tctcagccct   16860
ttgggagcca gtgggaaaat tgcttgggcc caggagttca aggttacagt gagctatgat   16920
ggcactactg ctctccagcc agtgcactca ctctgcacaa cagagtgaga ccctgtctct   16980
taaaaaaaaa aaaaaaaaaa ggccaggtgc agtggctcat gcctgtaatt ccagcacttt   17040
gggaggccga ggcgggcgga tcacaaggtc aggagttcaa gaccagcctg ccagcatggg   17100
tgaaaccctg tctctactaa aaatacaaaa aattagccag gcatggtggt gtgctcctgt   17160
```

```
attcccagct acttaggaag ctgaggcagg agaatcactt gaacccagga ggtggaggtt   17220
gcagtgagct gagattgctg ccactgtact ccagcctggg cgatagagca agactctgtc   17280
tcaaaaaaaa aaaaaaaaaa aaaaaaaaaa aaaggtcttc ctttcctatt tactcttatg   17340
gatacttatt ttattctagt caatggttat aatcctttac aatcattatt tattttagcc   17400
agcccctcca agttggctcc tgtgttcttt gggctgtacc cttaattctt tgagtcttgt   17460
cttgtttgca caagatgctc tgggcttata ttatatttcc cccatcccag ccatttctcc   17520
aaggaatgtt tccttttagt ggagaatgat atttagaaac caaatgctga ggctgggtgt   17580
gctcattgcc attgagttat acctttacct tattgactgg tttctactgt tctattcaga   17640
gacccctggc acaagatccc tgccctggac ccagagaagc tcaatgtctt ccggacagta   17700
cgggagatca caggtgagtg gcagagagtt tgcccttttct agaagaatag gtgaaccact   17760
ggcataaatt gcggtataac tacttgagaa atcacgtcc caagttatag gggaggagcc   17820
aggagaaccc aagaaagaag aaggctccct gcccatatgc ctctctccaa cccctcaggt   17880
tacctgaaca tccagtcctg gccgccccac atgcacaact tcagtgtttt ttccaatttg   17940
acaaccattg gaggcagaag cctctacaag tgagtaaagg gtatggagga aatggcatct   18000
tcaggcaatg aagcctgtgt cataggcatt ctttagtaaa atacaaggca ctgtctcata   18060
cagcagtgcc tcaaaaccaa agggtttcag agtttcacga ggaaaaggca aaaggagggg   18120
gattccctct cagtggatct gactagcact gagcaaattt cttgactaac atgaatcctt   18180
tgaatagtta atgttccctt agtagtctct cctctcatcc tgtctcctta ttctcagccg   18240
gggcttctca ttgttgatca tgaagaactt gaatgtcaca tctctgggct tccgatccct   18300
gaaggaaatt agtgctgggc gtatctatat aagtgccaat aggcagctct gctaccacca   18360
ctctttgaac tggaccaagg tgcttcgggg gcctacggaa gagcgactag acatcaagca   18420
taatcggccg cgcagagact gcggtgaggg aaagggtctg ctaggtggtg agaatagga   18480 gtcaggagag agagggctga aaggactatt ctgccctaga cgtgggagta gggttgaggg   18540
atggaaccaa ggagaagggg gctgttaggc tggaagcagt aacgaggaag aataatgaag   18600
agagggcttg ctgggagtcc tcagactcct ctcctaaccc acccccttcct ttccagtggc   18660 agagggcaaa gtgtgtgacc cactgtgctc ctctggggga tgctgggggc caggccctgg   18720
tcagtgcttg tcctgtcgaa attatagccg aggaggtgtc tgtgtgaccc actgcaactt   18780
tctgaatggg tacagtaagg ggagccagtc aaggatgggt gggggtgggg ccctgcaatg   18840
gaactgttca ggtggcatac aataaaagtc tttagacagc tttctgcatg tgccttggtg   18900
ggattgaggt aggagacctg tggttgtgag atcggagcat aaggtcagg acttggaagt   18960 gaccccccc tccctttatt ccccactaca gggagcctcg agaatttgcc catgaggccg   19020
aatgcttctc ctgccacccg gaatgccaac ccatggaggg cactgccaca tgcaatggct   19080
cggtatacta gtagcaccag gatctccaag ggagacagag aagggcaat acttggagca   19140 tctgggaat gatatggcta aggatagcac agagaggcca gataatgcta gggcctgcag   19200
atagaagatc ctgaatgtct gggttggtct ttgctgggag gtatggaatt gaccttggga   19260
tctgattctt cctgaccttc tctcttccac tcagggctct gatacttgtg ctcaatgtgc   19320
ccattttcga gatgggcccc actgtgtgag cagctgcccc catggagtcc taggtgccaa   19380
gggcccaatc tacaagtacc cagatgttca gaatgaatgt cggccctgcc atgagaactg   19440
cacccagggg tcagtgatgg gataataagg agaggggtc aggtgaagg gtaggagcac   19500 agaactagag tgagggaagc agaaagaaga gagaggctgt gattcaagaa tcactcccag   19560
```

```
ctggccgggc gcagtggctc acacctgtaa tcccagcact gtgggaggcc gaggtgggtg   19620
gatcacctga ggtcgggagt tcgagaccag cctgaccaat atggagaaac cctgtctcta   19680
ccaaaaattt aaaattagcc cggcgtggtg gcgcatgcct gtaatcccag ctacgcggga   19740
ggctgaggca ggagaatttc ttgaacccag gaggcagagg ttgcggtgag ctgagattgc   19800
atcattgtac tccagcctgg gcaacaagag tgaaactctg tctcaaaaaa aaaaaagaa    19860 tcactcccag ctgtgtagcg aaggattgga gaaagggaaa atcagtaaca gcacaaaatt   19920
acaccacagt tttgggaacc tggaataacc tcagttcaag ggagtttcac agaagagggg   19980
cttggggaga gctagtgagc tggaggtgga ggccatgtct tgggatcagc tctgggctcc   20040
aggatgggat gccacggtaa gttctgaaac aagcttttat atgttaggct gttgaaattg   20100
agcctctgct gtccaagctc tcatttaagg tggtgacttt cttccctagg tgtaaaggac   20160
cagagcttca agactgttta ggacaaacac tggtgctgat cgggtatgat ggggttggag   20220
attctggaaa ctggggatat ttgggagttg gagagaggt ggttacctgg agaagagg    20280 gaggctgtct tcattctggc cttttatgta tgcagtccac tatcactgga cacttgggac   20340
tcaagaatgc aggcttctgg acttcccttc ctaaaattaa ctttcagtag tctaagactg   20400
gtccagattt aggttggtcc cttcagtgct taaggatata tatgtgaatg ttaatttctt   20460
gccccaggtc agcatcatac cttcaacaca agtatagttg acatttgtaa ggaagatgca   20520
aacccaggat aatgttgggt ttctatatat cccatagcaa aacccatctg acaatggctt   20580
tgacagtgat agcaggattg gtagtgattt tcatgatgct gggcggcact tttctctact   20640
ggcgtgggcg ccggattcag aataaaaggg ctatgaggcg atacttggaa cggggtgagg   20700
tgagtactta gcttactttt gtttttttctt ttcttttttt gcatgtcctg gaagtctctt   20760
tatagcttaa ttttgagtgg taccctgtgc acccaggggt cagtgatggg ataaatgtca   20820
ctcccctcct ctttcccag agatttgatc cctttcttca aggaagtagt gtggtcccct   20880
agaagaacac tggtcagaga aatgggaggc atgcattcta gtcctgatt tgccattaat     20940 ttgccacatg actttgaaga agttacttat cttctctgtg cctcggttta tgcatctata   21000
cagaggaaat aacatttgtc cttccaggat ggctgtaagg gtaaaggggg atgatgtatg   21060
tgaaagtgct ttggaaagca cagagcactg tataaaaggt actcaaggtg gtaatagtac   21120
taccaactct ccctagctgt ccccttcccc actttgtgct cctccatcaa agggaaaacc   21180 caacccctt gattcctgat ctcatgagca caaataactt cctcagttct cagggtctgt     21240
acctcaatat gcctataatc cattccagga ctaacggtgc ttcctcttcc tgcccttca    21300 gctgtgctgc ttttggcatt cacctatgag gagcgggttg gagtgggaca tgggaatggc   21360 cttcctgag taactccttc ccatttgctc ctcagagcat agagcctctg gaccccagtg    21420
agaaggctaa caaagtcttg gccagaatct tcaaagagac agagctaagg aagcttaaag   21480
tgcttggctc gggtgtcttt ggaactgtgc acaaagtgag tgacccatag gaattctgga   21540
gaggtgggga aggcatctag ggcaaagggg tgaaagattt ttgcatagga ttgacctagg   21600
gagaatgacc ttatgccaac tcctgcccca aacttcccag ggagtgtgga tccctgaggg   21660
tgaatcaatc aagattccag tctgcattaa agtcattgag acaagagtg gacggcagag    21720 ttttcaagct gtgacagatg taagtgaagg aaattctgta tgccgctagg agagaggaca   21780
atattagata caatcatgta gaagcagggt cctgtgcttc tcagcagcta ctatgttagc   21840
cagaatgttg ggggtggggg ggcctgggct ggctgtgcac atgctgagtg tatgtgaacc   21900
```

```
tgttggtttc ctagataata cctttttgtgt ctcttagcat atgctggcca ttggcagcct   21960
ggaccatgcc cacattgtaa ggctgctggg actatgccca gggtcatctc tgcagcttgt   22020
cactcaatat ttgcctctgg gttctctgct ggatcatgtg agacaacacc ggggggcact   22080
ggggccacag ctgctgctca actggggagt acaaattgcc aaggtgagag aagcctggag   22140
gaattctgtg ataagaactg cttgtctggg ggccagccag gaaaaagtga aaggttgaa   22200 gttctgagag gtgaggtccc aaccccccgg gctgcagact ggtaccagtc catggcctgt   22260
taggaaccag gccacagagc atgtgagcgg caggcaagcg agtgaagctt catctgtatt   22320
tacagtcagt ccccatcact tgcattaccg cccgagttcc gcctcctgtc agatcagggg   22380
cagcattaga ttctcttagg agcttgactt ctattgtgaa ctgtgcatgt gaaggatcta   22440
ggttgtgcac tccttatgag aatctaacta atgcctgatg atctgaggtg gaaaaatttc   22500
atcccaaaac caaccctccc cttcccctgg aaaaactgtc ttccacaaaa ccagtccctg   22560
gtgccaaaaa aggttgggga ccactgctga gaggtacctt caagatttgg gggaattcca   22620
gatctcagtg actgattccc ccaaccttaa gaatactttc ttccccctata cctacaggga   22680 atgtactacc ttgaggaaca tggtatggtg catagaaacc tggctgcccg aaacgtgcta   22740
ctcaagtcac ccagtcaggt tcaggtggca gattttggtg tggctgacct gctgcctcct   22800
gatgataagc agctgctata cagtgaggcc aaggtgagga gacacaaagg gtaaggaggc   22860
gggggtggag tgaagcatgg ggataggggag cagccagtgg tctcttccag aggcaagcag   22920
atgcttcatg gtaagttcaa ggagagaagg ctgcagatgc cagatatttt agttcagagg   22980
gcaacaaata aaataatgat caagaacttg ggactggccg ggcgcggtgg ctcacgcctg   23040
taatcccaac acttcgggag gccaaggcgg gtggatcaca aggtcaggag atcaagacca   23100
tcctggctag cacggtgaaa ccccgtctct actaaatata caaaaaaaaa aaaaattagc   23160
caggcgtggc ggcatgcatc tgtactccca gctactcggg aggctgaggc aggagaatgg   23220
cgtgaaccca ggaggcggag cttgcagtgg gccgagatcg caccactgca ctccagtctg   23280
ggcgacagag cgagactccg tctcaaaaaa aaaaaaaaa gaatttggga cttggaaatc   23340
ctaagaaaat ttgtggaaat aaacttgtga tacctctatc tttaatccgc agactccaat   23400
taagtggatg gcccttgaga gtatccactt tgggaaatac acacaccaga gtgatgtctg   23460
gagctatggt cagtgcatct ggatgccctc tctaccatca ctggcccag tttcaaattt   23520 accttttgag accccctctt agaatctcta agcacttcag attttttgtgt tagatcaggt   23580 tctgccttcc cttcacttca tgcccatgtc tactattttg ccagtgacta gtccatgtct   23640
tcctgcaaca ggtgtgacag tttgggagtt gatgaccttc ggggcagagc cctatgcagg   23700
gctacgattg gctgaagtac cagacctgct agagaagggg gagcggttgg cacagcccca   23760
gatctgcaca attgatgtct acatggtgat ggtcaagtgt gagttacctg ctgagcccaa   23820 ccatttctc ttttttttctt ttttttttctt ttttttttttt ttttgagaca gagtctcaca   23880
attgtcaccc aggctggagt gcaatggtgc aatcaatctt ggctcactac aacctccgcc   23940
tctcgggttc aagagattct cctgcttcag cctccggagt agctgggatt acaggcgccc   24000
gccacacctg gataactgtt acacttttag tagagatggg gtttcaccat gttggccagg   24060
ctggtctcaa actcctgacc tcaggtgatc cgcctgcctc agcttcccaa agtgctggga   24120
ttacaggtgt gagccatcat gctcggcctg actgcagcca ttttctgact tccctctgta   24180
ctcctcttat ggctctattc cttttttttttt tatggagtct cgctctgttg cccatactgg   24240
agtgcagtag cgtgaccttg gctcaccgtg acctccacgt tccaggttta agttcttctg   24300
```

```
tctcagcctc ccagatagct gggactttag gcgtgcacca ccacgcccag ctaattttt   24360 tttgtctttt tagtagagat ggggtttcac tatgttggcc aggctggtct caaagtcccg   24420
acctcaggtg atccacccgc cttggcctcc caaagtgctg ggattatagg tgtgagccac   24480
cgcgcccggc catggaatgt attctctttt atgtctctac ctcctacatc ttatctccag   24540
gttggatgat tgatgagaac attcgcccaa cctttaaaga actagccaat gagttcacca   24600
ggatggcccg agaccacca cggtatctgg tcataaaggt gagtagggag taggaggtgc   24660
taaggaaatt tagaaaaagg aggagttggc tggaaccagg attcccccta acaatcacct   24720
atcgatatag agagagagtg ggcctggaat agcccctggg ccagagcccc atggtctgac   24780
aaacaagaag ctagaggaag tagagctgga gccagaacta gacctagacc tagacttgga   24840
agcagaggag acaacctgg caaccaccac actgggctcc gccctcagcc taccagttgg   24900
aacacttaat cggccacgtg gggtaagaca acttctaatt acccaacact ttgcaccctg   24960
agccctcaca aaccctacag atacccagat taactactca aaggccccca tggtgaatgt   25020
agatttctcc cttcatctta acctttcct tatttttca tcctagagcc agagccttt    25080 aagtccatca tctggataca tgcccatgaa ccagggtaat cttggggagt cttgccaggt   25140
aagttctgtt gctgagaggc tgggttttag gatcagattg atacgagtag tatggaagac   25200
attagaaacc tctgaggttt aatcagtgtc ctgcaaaaaa gaaggcagtg agggccgggc   25260
gagttggctc acacctgtaa tcccagcact ttgggaggcc agagagagtg gatcacctga   25320
ggttaggagt ttgagaccag cctggccaac atggtgaaac cccgtctcta cccaaaatac   25380
aaaaattagc tgggtgtggt ggtgcacacc tgtaatcaca gctactcagg aggctgagac   25440
aggagaatcg cttgaacccg ggaggcagag gttgcagtga gctgagattg taccactgca   25500
ctccagcctg ggtgacagag caagaccctg tctcttaaaa aaaaaaaaa aaggccaggt   25560 gcggtggctc acgcctgtaa tcctagcact ttgggaggcc gaggtgggcg gatcatgagg   25620
tcaggagttc gagaccagcc tgaccaacat ggcaaaaccc tgtctgtact aaaaatacaa   25680
aaactagctg cacatgatgg caggtgcctg taatcccagc tactcgggag gctgaggcag   25740
gagaatcact tgaacaggga agcagaggct gcagtgagcc aagataatgc cactgcactc   25800
cagcctgggc gacaagaaca agactccacc tcaaaaaaa aaaaaaaaa aaaaaaggc   25860 agtgaacaac ccaatatcct tctaaacaaa tctctcttct ttcctcatca tgtaaattc   25920 cttgcattat tttctgttta ttttcttcct taggagtctg cagtttctgg gagcagtgaa   25980
cggtgccccc gtccagtctc tctacaccca atgccacggg gatgcctggc atcagagtca   26040
tcagaggggc atgtaacagg ctctgaggct gagctccagg agaaagtgtc aatgtgtagg   26100
agccggagca ggagccggag cccacggcca cgcggagata gcgcctacca ttcccagcgc   26160
cacagtctgc tgactcctgt taccccactc tccccacccg ggttagagga agaggatgtc   26220
aacggttatg tcatgccaga tacacacctc aaaggtgcct gactcttcct agggcttttcc   26280 tcaattttc ctcgaattct ttccccgggc tcctctttt tcttctctga tcatatgcct   26340
ctctgtccta ttaattttt caaactttcc cctaccctca tgaagttctt cacataccta   26400
gcctttcttc tcaaccccca ggtactccct cctcccggga aggcacctt tcttcagtgg   26460 gtctcagttc tgtcctgggt actgaagaag aagatgaaga tgaggagtat gaatacatga   26520
accggaggag aaggcacagt ccacctcatc cccctaggcc aagttcccctt gaggagctgg   26580 gttatgagta catggatgtg gggtcagacc tcagtgcctc tctgggcagc acacagagtt   26640
```

```
gcccactcca ccctgtaccc atcatgccca ctgcaggcac aactccagat gaagactatg  26700
aatatatgaa tcggcaacga gatggaggtg gtcctggggg tgattatgca gccatggggg  26760
cctgcccagc atctgagcaa gggtatgaag agatgagagc ttttcagggg cctggacatc  26820
aggcccccca tgtccattat gcccgcctaa aaactctacg tagcttagag gctacagact  26880
ctgcctttga taaccctgat tactggcata gcaggctttt ccccaaggct aatgcccaga  26940
gaacgtaact cctgctccct gtggcactca gggagcattt aatggcagct agtgccttta  27000
gagggtaccg tcttctccct attccctctc tctcccaggt cccagcccct tttcccagt   27060 cccagacaat tccattcaat ctttggaggc ttttaaacat tttgacacaa aattcttatg  27120
gtatgtagcc agctgtgcac tttcttctct ttcccaaccc caggaaaggt tttccttatt  27180
ttgtgtgctt tcccagtccc attcctcagc ttcttcacag gcactcctgg agatatgaag  27240
gattactctc catatccctt cctctcaggc tcttgactac ttggaactag gctcttatgt  27300
gtgcctttgt ttcccatcag actgtcaaga agaggaaagg gaggaaacct agcagaggaa  27360
agtgtaattt tggtttatga ctcttaaccc cctagaaaga cagaagctta aaatctgtga  27420
agaaagaggt taggagtaga tattgattac tatcataatt cagcacttaa ctatgagcca  27480
ggcatcatac taaacttcac ctacattatc tcacttagtc ctttatcatc cttaaaacaa  27540
ttctgtgaca tacatattat ctcattttac acaagggaa gtcgggcatg gtggctcatg   27600
cctgtaatct cagcactttg ggaggctgag gcagaaggat tacctgaggc aaggagtttg  27660
agaccagctt agccaacata gtaagacccc catctcttta aaaaaaaaa aaaaaaaaa    27720 aaaaaaactt tagaactggg tgcagtggct catgcctgta atcccagcca gcactttggg  27780
aggctgagat gggaagatca cttgagccca gaattagaga taagcctatg gaaacatagc  27840
aagacactgt ctctacaggg gaaaaaaaaa aagaaactg agccttaaag agatgaaata   27900
aattaagcag tagatccagg atgcaaaatc ctcccaattc ctgtgcatgt gctcttattg  27960
taaggtgcca agaaaaactg atttaagtta cagcccttgt ttaaggggca ctgtttcttg  28020
tttttgcact gaatcaagtc taaccccaac agccacatcc tcctatacct agacatctca  28080
tctcaggaag tggtggtggg ggtagtcaga aggaaaaata actggacatc tttgtgtaaa  28140
ccataatcca catgtgccgt aaatgatctt cactccttat ccgagggcaa attcacaagg  28200
atccccaaga tccacttta gaagccattc tcatccagca gtgagaagct tccaggtagg   28260
acagaaaaaa gatccagctt cagctgcaca cctctgtccc cttggatggg gaactaaggg  28320
aaaacgtctg ttgtatcact gaagttttt gttttgtttt tatacgtgtc tgaataaaaa   28380
tgccaaagtt ttttttcagc ttcctgtctg tcaaatgaag acatttcgta tgttagataa  28440
gagatctgct cctcagcagt ggatactcac cttctgtgt tctgacagtg ctactctgtc    28500
ccatgcagct ttctctagtc ctactattac ttctatttct ttagaacaac catagcgcat  28560
agtccttttc attaagggtt ttagtaggaa tctacaaggc aaccaattgg gaataacaaa  28620
aagaacctac gtgctttagg acttataaaa agccctataa gccctccttc agaggccaaa  28680
cactgaaacc tccagatgct tctgaattca ttatcttaga aaagtcatca aatctttta    28740 ttttttcacg gtaagaactc tcaacaaaca tgtctttctg aacacttccc ttaggtgctc  28800
catccaggtg cctgttattg gaacaataaa gtcatgttac ttcattagga gtccggcctc  28860
tagattgcga ggccttaaa tggatgatcc ctccggtgtc tggctgccca gttagccccc   28920
gttaccagca cccttggtct tcttccacct gtctgccct cctgttctc ccagcttcgg    28980 aggacgactg gaccggctgg gcgggtttcg ccagccgacc cagggatccg aagaagggcg  29040
```

-continued

```
cacccagcct ccccgaccta ggtgtagaca ctgcccaccc gctgcggctc cactctactc    29100
cacccctgcc cgctcgactt taaacctatt tccccgccgt agctccgccc ctctcccctc    29160
agcccgcccc tctctgttac tggctctcgc tcagcgttct cggtggaagt ggtttttccg    29220
ggagagacca cgcttcccct caagctcccc aacggctccg ccttcccgcc ggagcctgac    29280
ccttcccaga gtgcccggcg attccggcgt gcgaggccct tggagggcaa ggccccaggg    29340
cctggcttag gagcgcgaga ggcaggctgg gaattgtagt tcgaaggccc tcgagagcgg    29400
ctagagtctg gcggccgaga ggactagttg tcccagcgtg ccctgcgcct cagcccgcgc    29460
gctcgcagct tctcgctctc gcctgcctgc ccgctccctt gcttgctcgc gctttcgctc    29520
gccctctcct cgaggatcga ggggactctg accacagcct gtggctggga agggagacag    29580
aggcggcggc ggctcagggg aaacgaggct gcagtggtgg tagtaggaag atgtcgggcg    29640
aggacgagca acaggagcaa actatcgctg aggacctggt cgtgaccaag tataagatgg    29700
ggggcgacat cgccaacagt gagtgcggcc tcggggtcg gggaatcaag gctgataggg    29760
aaaggtaaca ggctggcccg gaaggggctg gagcggaggg gtcatgcgga ctgagctact    29820
gaggggcccg caccggtccg ctgggcacgg cgtggtggga agacccggtg tcgcgcctgg    29880
gacctgagcg ggcaggccca ggctgaagtc tatggaggtg cgggtcggcg accaggatga    29940
gcgcagagag gggaccctgg caggctccga cccgaggccg tttgttagga ggcaagacgt    30000
gttttctctt gttcctatcc ttcattcccg attattgctt cctctgattc tggcagcggc    30060
gaggccacct cgaaaaggaa gcgcccagct attggcgaca gaagtgcccc tctgtttttg    30120
tagcgtctcc ggggcgtcag gagccaagcc ggcacgtgtt gctgggtccc attgcggatg    30180
gctggccccc ttcttactcc gctagtgtcc ctgacaccag cttccccacc accagct      30237
```

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 5

Asn Leu Arg Val Val Arg Gly Thr Gln Val Tyr
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 6

Asp Lys Leu Cys His Met Asp Thr Ile Asp Trp Arg Asp Ile Val
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 7

```
Pro Cys His Glu Val Cys Lys
1               5

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 8

Ile Cys Ala Pro Gln Cys Asn Gly His Cys Phe Gly Pro Asn Pro
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 9

Asn Gly Asp Pro Trp His Lys
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 10

Asp Pro Leu Cys Ser Ser Gly Gly Cys Trp Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 11

Cys Pro His Gly Val Leu Gly Ala Lys Gly Pro
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 12

Ile Ala Gly Leu Val Val Ile Phe Met Met Leu Gly Gly Thr Phe
1               5                   10                  15

<210> SEQ ID NO 13
<211> LENGTH: 11
<212> TYPE: PRT
<213> ORGANISM: Artificial Sequence
```

```
<220> FEATURE:
<223> OTHER INFORMATION: Synthetic peptide derived from HER3 protein
      sequence

<400> SEQUENCE: 13

Leu Glu Arg Gly Glu Ser Ile Glu Pro Leu Asp
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 14

Gln Leu Leu Tyr Ser Glu Ala Lys Thr Pro Ile
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 15

Glu Ser Ile His Phe Gly Lys Tyr Thr His Gln Ser Asp Val Trp
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 16

Val Trp Glu Leu Met Thr Phe Gly Ala Glu Pro Tyr Ala Gly Leu
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 17

Glu Ser Gly Pro Gly Ile Ala Pro
1               5

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 18

Thr Leu Asn Arg Pro Arg Gly Ser Gln Ser Leu Leu Ser Pro Ser
1               5                   10                  15
```

```
<210> SEQ ID NO 19
<211> LENGTH: 15
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 19

Glu Ala Glu Leu Gln Glu Lys Val Ser Met Cys Arg Ser Arg Ser
1               5                   10                  15

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 20

Glu Glu Asp Val Asn Gly Tyr Val Met Pro Asp
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 21

Met Pro Thr Ala Gly Thr Thr
1               5

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide derived from HER3 protein
      sequence

<400> SEQUENCE: 22

Asp Gly Gly Gly Pro Gly Gly Asp Tyr Ala Ala Met
1               5                   10

<210> SEQ ID NO 23
<211> LENGTH: 35
<212> TYPE: DNA
<213> ORGANISM: Artificial Sequence
<220> FEATURE:
<223> OTHER INFORMATION: Synthetic primer: hHER3-F

<400> SEQUENCE: 23
cagggcggcc gcaccatgag ggcgaacgac gctct                              35

<210> SEQ ID NO 24
<211> LENGTH: 37
<212> TYPE: DNA
<213> ORGANISM: Artificial Sequence
<220> FEATURE:
<223> OTHER INFORMATION: Synthetic primer: hHER3-ECDTM-R

<400> SEQUENCE: 24
acaagcggcc gcagttaaaa agtgccgccc agcatca                            37
```

```
<210> SEQ ID NO 25
<211> LENGTH: 39
<212> TYPE: DNA
<213> ORGANISM: Artificial Sequence
<220> FEATURE:
<223> OTHER INFORMATION: Synthetic primer: hHER3-ECD-R

<400> SEQUENCE: 25
acaagcggcc gcatttatgt cagatgggtt ttgccgatc                              39

<210> SEQ ID NO 26
<211> LENGTH: 33
<212> TYPE: DNA
<213> ORGANISM: Artificial Sequence
<220> FEATURE:
<223> OTHER INFORMATION: Synthetic primer: hHER3-ECDC1C2-R

<400> SEQUENCE: 26
acaagcggcc gcattgtcag atgggttttg ccg                                    33
```